(12) United States Patent
Lai

(10) Patent No.: US 10,595,724 B2
(45) Date of Patent: Mar. 24, 2020

(54) ADAPTOR FOR AN IMAGE CAPTURE DEVICE FOR FUNDUS PHOTOGRAPHY

(71) Applicant: Ho Wa Lai, Sham Tseng (CN)

(72) Inventor: Ho Wa Lai, Sham Tseng (CN)

(*) Notice: Subject to any disclaimer, the term of this patent is extended or adjusted under 35 U.S.C. 154(b) by 306 days.

(21) Appl. No.: 15/669,210

(22) Filed: Aug. 4, 2017

(65) Prior Publication Data

US 2019/0038132 A1 Feb. 7, 2019

(51) Int. Cl.
| | | |
|---|---|---|
| *A61B 3/10* | (2006.01) | |
| *A61B 3/14* | (2006.01) | |
| *A61B 3/00* | (2006.01) | |
| *A61B 3/12* | (2006.01) | |
| *G02B 7/02* | (2006.01) | |
| *G02B 7/04* | (2006.01) | |
| *G02B 13/00* | (2006.01) | |

(52) U.S. Cl.
CPC .............. *A61B 3/14* (2013.01); *A61B 3/0008* (2013.01); *A61B 3/12* (2013.01); *G02B 7/021* (2013.01); *G02B 7/04* (2013.01); *G02B 13/001* (2013.01)

(58) Field of Classification Search
CPC ........... A61B 3/14; A61B 3/0008; A61B 3/12; A61B 3/1025; A61B 3/1233; A61B 3/1241; A61B 3/145; A61B 3/0016; G02B 13/001; G02B 7/04; G02B 7/021
USPC ....................................................... 351/206
See application file for complete search history.

(56) References Cited

U.S. PATENT DOCUMENTS

| | | |
|---|---|---|
| 6,019,472 A | 2/2000 | Koester et al. |
| 8,118,428 B2 | 2/2012 | Yogesan et al. |
| 10,105,051 B2 | 10/2018 | Gupta |

(Continued)

FOREIGN PATENT DOCUMENTS

| | | |
|---|---|---|
| WO | 2015054672 A1 | 4/2015 |
| WO | 2015100294 A1 | 7/2015 |

(Continued)

OTHER PUBLICATIONS

D-eye www.d-eyecare.com; News Release—Apr. 18, 2017.

(Continued)

*Primary Examiner* — William R Alexander
*Assistant Examiner* — Henry A Duong
(74) *Attorney, Agent, or Firm* — Bond Schoeneck & King, PLLC; George McGuire

(57) ABSTRACT

An adaptor for attachment to an image acquisition device, the image acquisition device having one or more camera apertures for enabling capture of one or more images entering the image acquisition device via the one or more camera apertures. The adaptor has a housing defining a passage along which light waves may travel, an objective lens arrangement within the passage, a secondary lens arrangement within the passage positioned such that, when the adaptor is attached to an image acquisition device, the secondary lens arrangement is along a possible light pathway between the objective lens arrangement and one or more camera apertures. The lens arrangements are together configured to magnify an image of a pupil of the eye in proximity to a plane of one or more camera apertures and to focus light waves from a light source at a point external of the adaptor and offset from the optical axis of the objective lens.

18 Claims, 19 Drawing Sheets

(56) References Cited

U.S. PATENT DOCUMENTS

| | | | |
|---|---|---|---|
| 2008/0106696 A1* | 5/2008 | Buckland | A61B 3/102 |
| | | | 351/206 |
| 2012/0320340 A1 | 12/2012 | Coleman, III | |
| 2013/0057828 A1 | 4/2013 | Furuhaski | |
| 2013/0083182 A1 | 4/2013 | Kitano | |
| 2014/0085603 A1 | 3/2014 | Su et al. | |
| 2014/0267668 A1* | 9/2014 | Ignatovich | A61B 3/14 |
| | | | 348/78 |
| 2016/0296111 A1* | 10/2016 | Russo | A61B 3/12 |

FOREIGN PATENT DOCUMENTS

| | | |
|---|---|---|
| WO | 2016040935 A1 | 3/2016 |
| WO | 20180043657 | 3/2018 |

OTHER PUBLICATIONS

Volk iNview https://volk.com/index.php/volk-products/opthalmic-cameras/volk-inview.html.
WelchAllyn iExaminer; htttps://www.welchallyn.com/content/welchallyn/americas/en/microsites/iexaminer.html.
Digisight—https://www.digisight.net/ds/.
International Search Report and Written Opinion for No. Application PCT/IB2018/055756, from the State Intellectual Property Office of the P.R. China, pp. 1-10, dated Oct. 31, 2018.
Application No. EP 17 19 1914, European Search Report, pp. 1-10, dated May 16, 2018.

* cited by examiner

ADAPTOR FOR AN IMAGE CAPTURE DEVICE FOR FUNDUS PHOTOGRAPHY

FIELD OF THE INVENTION

The present invention relates to an adaptor for an image capture device for fundus photography and, in particular, but not exclusively, relates to an adaptor for a smartphone to enable the smartphone to capture images of the fundus of an eye that would otherwise not be possible by the smartphone.

BACKGROUND OF THE INVENTION

FIG. 1 shows the basic structure of a human eye 1 which comprises a cornea 3, a pupil 5, a lens 7, and a retina 9. The retina 9 is an internal light sensitive layer at the back of the eye 1 and is primarily responsible for vision. Light from a distant object or light source 11 travelling in a near parallel path enters the eye through the pupil 5 and is focused at a point on the retina 9 by the refractive power of the cornea 3 and lens 7. The light focussed on the retina 9 is detected by photoreceptor cells of the retina 9, and converted into an electrical signal. The electrical signal is transferred by retinal ganglion cells, through the optic nerve of the eye 1, into the brain for visual processing. This is generally how a human can see the outside world.

Unlike the cornea 3, the retina 9 is currently not replaceable. Currently there is no artificial retina or other substitutes that can provide sufficient visual function in the event the retina fails. Unfortunately, the retina 9 is quite vulnerable to various problems and diseases and is therefore subject to failure. Consequently, care should be taken to ensure the health of the retina. Furthermore, since the retina is the only portion of the central nervous system visible from outside the human body, inspection of the retina can enable detection of other health issues such as diabetes. Therefore, examination of the retina 9 is one of the most important aspects of an eye examination because it enables the detection and prevention of pathological conditions that can result in irreversible visual loss or other health related issues.

An eye examination is traditionally carried out by a specialist eye doctor, commonly referred to as an ophthalmologist, who visually inspects the fundus of the eye using an ophthalmoscope. One limitation of an ophthalmoscope is that it is unable to contemporaneously record visual details of the fundus which means that the ophthalmologist is required to subsequently document his findings of the visual inspection of the retina in text or drawings. Accurate recording or documentation of images of the fundus require another instrument commonly referred to as a retinal camera or fundus camera. The process of taking photographs of the retina is called fundus photography. Fundus photography provides photographic documentation of the retina and facilitates documentation, monitoring, case discussion, mass screening, and even telemedicine.

Conventional fundus cameras are usually large machines that must be table mounted and connected to a desktop computer system for image storage and organisation. Such conventional cameras are not helpful for bed-bound patients, infants and children, or other patients that cannot easily move or cooperate for accurate positioning relative to the camera. Furthermore, such cameras limit the examination to the clinic or hospital. Outreach screening with such fundus cameras is therefore very difficult.

Recently, a number of portable fundus cameras have been developed to address these mobility issues. These portable fundus cameras have greatly expanded the ability to conduct funduscopic or ophthalmoscopic examinations. However, portable fundus cameras still require relatively complicated connection to a computer system for photo storage, processing and organisation. Auto-analysis and telemedicine is possible with such cameras, but is still limited to specialist centres that have the dedicated facilities and computer systems for assessment.

With the advent of smartphones and other portable image acquisition devices, retinal imaging with smartphones is gaining popularity. One advantage of using a smartphone for retinal imaging is that it does not require connection to remote computer systems. Smartphones also allow instant image capture, review, analysis, organisation and sharing of fundus photographs. As smartphones are popular among health care professionals, every suitably qualified health care professional with a smartphone and an appropriate adaptor has the necessary technology to perform fundus photography.

Apart from the ease of use, there are many additional advantages of using a smartphone and adaptor to take photographs of the fundus. With constant improvements in smartphone camera technology, the resolution of fundus photographs will correspondingly improve. Various smartphone software can also be developed by third parties to further improve diagnostic performance and facilitate patient care. As modern smartphone cameras can offer high light sensitivity, smartphones can be used to take fundus photographs under lower illumination levels than traditional ophthalmoscopy apparatus.

There are a number of such adaptors on the market. However, most of them offer a limited field of view (at most around 50 degrees of view). This limited field of view can only show the central part of the retina. In order to provide a more comprehensive screening of the retina, a much wider field of view is needed. On the other hand, the adaptor should be small and lightweight to facilitate portable clinical use.

It is an object of the present invention to provide an improved adaptor for a portable image acquisition device for fundus photography with a wider field of view.

SUMMARY OF THE INVENTION

In accordance with a first aspect of the present invention, there is provided an adaptor for attachment to an image acquisition device, the image acquisition device having one or more camera apertures for enabling capture of one or more images entering the image acquisition device via the one or more camera apertures, the adaptor comprising
a housing defining a passage, the housing configured to permit light waves to enter one or more camera apertures of the image acquisition device from the adaptor exterior via the passage and to permit light waves to exit the passage to the adaptor exterior,
an objective lens arrangement within the passage having an optical axis, a front focal point, and a back focal point,
a secondary lens arrangement within the passage having an optical axis, a front focal point, and a back focal point, the secondary lens arrangement positioned in the passage such that, when the adaptor is attached to an image acquisition device, the secondary lens arrangement is along a possible light pathway between the objective lens arrangement and one or more camera apertures of the image acquisition device,
wherein a diameter of the secondary lens arrangement is greater than or equal to a diameter of the objective lens arrangement, wherein the objective lens arrangement and the secondary lens arrangement are together configured to magnify an image of a pupil of the eye in proximity to a plane of one or more camera apertures of the image acquisition device when the pupil of an eye is positioned so that the pupil plane substantially coincides with the front focal point of the objective lens, the magnified image of the pupil having a diameter which is dependent on the respective focal lengths and relative spacing of the objective and secondary lenses, at least one of the one or more camera apertures positioned within the diameter of the magnified image when the adaptor is attached to an image acquisition device, and wherein the objective lens arrangement and the secondary lens arrangement are together configured to focus light waves from a light source directed into the passage toward the secondary lens from a position in proximity to one or more camera apertures, offset from the optical axis of the secondary lens and within the diameter of the magnified image of the pupil, said light waves focussed at a point external of the adaptor and offset from the optical axis of the objective lens.

Advantageously, an adaptor according to the present invention may be attached to an image acquisition device such as smartphone with image capture capabilities to enable the smartphone to capture images of objects positioned in close proximity to the smartphone with a wide field of view. Thus, when the adaptor is attached to a smartphone with image capture capabilities, the smartphone may be used to capture images of a wide field of view of the retina of an eye when the eye is in close proximity to the adaptor and smartphone. Due to the configuration of the optical system of the adaptor in relation to an appropriately positioned light source, the adaptor may be positioned such that illumination light enters the pupil at the periphery of the pupil when the optical axis of the adaptor is aligned with the optical axis of the lens of an eye such that back scatter at the pupil plane due to illumination light from the adaptor is advantageously minimised. Therefore, an adaptor of the present invention permits images of the retina with a wide field of view to be captured by a smartphone without illumination light of the adaptor substantially interfering with a viewing pathway for light waves exiting the eye and into the adaptor for capture by the smartphone.

The adaptor may further comprise the light source. Additionally or alternatively, the light source may be separate from the adaptor and the adaptor may be configured to permit light from the light source to enter the passage. The light source may comprise one or more light emitting diodes.

The adaptor may further comprise one or more polarizers associated with the light source to polarise light from the light source and one or more other polarizers arranged to filter light entering one or more camera apertures from the passage when the adaptor is attached to an image acquisition device. The one or more polarizers may be associated with the light source polarises light differently from the one or more other polarizers so that polarised light from the light source is filtered out by the one or more other polarizers.

The secondary lens arrangement may be positioned such that, when the adaptor is attached to an image acquisition device, the back focal point of the secondary lens is located in proximity to the plane of one or more camera apertures of the image acquisition device so that the image acquisition device can focus the light waves received from the passage of the adaptor and capture one or more images.

The objective lens arrangement may have a shorter focal length than the secondary lens arrangement.

The objective lens arrangement may be positioned relative to the secondary lens arrangement such that the back focal point of the objective lens arrangement at least substantially coincides with the front focal point of the secondary lens arrangement.

The objective lens may be moveable relative to the secondary lens such that the position of the back focal point of the objective lens can be adjusted relative to the position of the front focal point of the secondary lens.

The objective lens arrangement and the secondary lens arrangement may each comprise a condensing lens. The objective condensing lens and the secondary condensing lens may each comprise a pair of doublet lenses, for each pair, the doublet lenses being arranged such that their more convex sides face toward one another.

The adaptor may further comprise a means for attaching the adaptor to the image acquisition device.

The image acquisition device to which the adaptor is intended to be attached may be a smartphone or tablet computer.

In accordance with a second aspect of the present invention, there is provided a fundus photography system comprising an image acquisition device and an adaptor according to the first aspect. The image acquisition device may be associated with a mounting device comprising means for attaching the adaptor to the mounting device to hold the adaptor in a position relative to the image acquisition device at which an optic axis of the adaptor is at least substantially aligned with an optic axis of the camera aperture of the image acquisition device. The mounting device may comprise a protective case for attachment to the image acquisition device. The means for attaching may comprise one or more magnets.

In accordance with a third aspect of the present invention, there is provided a method of using a fundus photography system according to the second aspect, comprising the steps of arranging the system such that the front focal point of the objective lens substantially coincides with the pupil plane of the pupil of an eye and such that the centre of the pupil is substantially aligned with the optical axis of the objective lens, directing light into the passage toward the secondary lens from a position in proximity to one or more camera apertures of the image acquisition device, offset from the optical axis of the secondary lens and within the diameter of the magnified image of the pupil, and capturing with the image acquisition device an image of a retina of the eye received by the image acquisition device from the eye interior via the adaptor.

BRIEF DESCRIPTION OF THE DRAWINGS

Preferred embodiments of the present invention will be explained in further detail below by way of examples and with reference to the accompanying drawings, in which:—

DETAILED DESCRIPTION OF THE PREFERRED EMBODIMENTS

Figure 1:
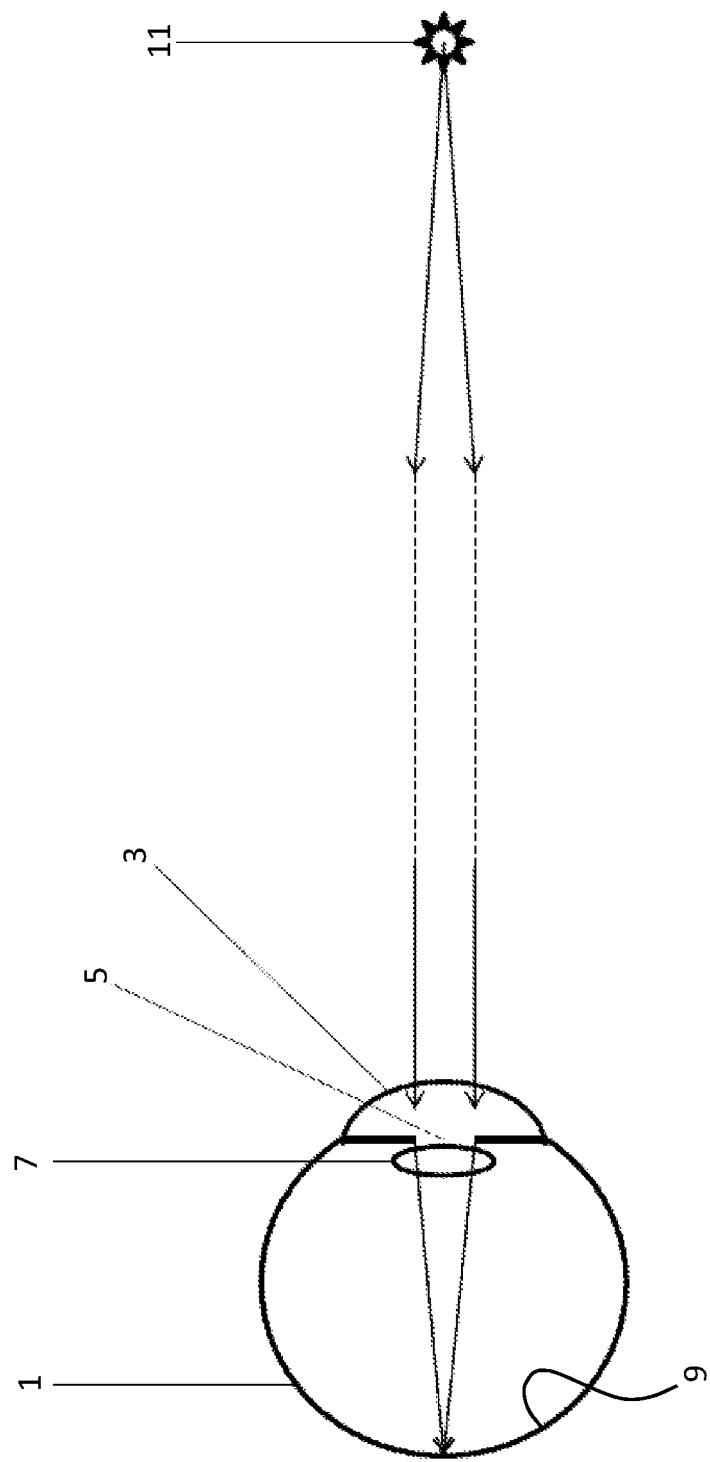
FIG. 1 shows a cross section of an eye receiving light from a light source.
Figure 2:
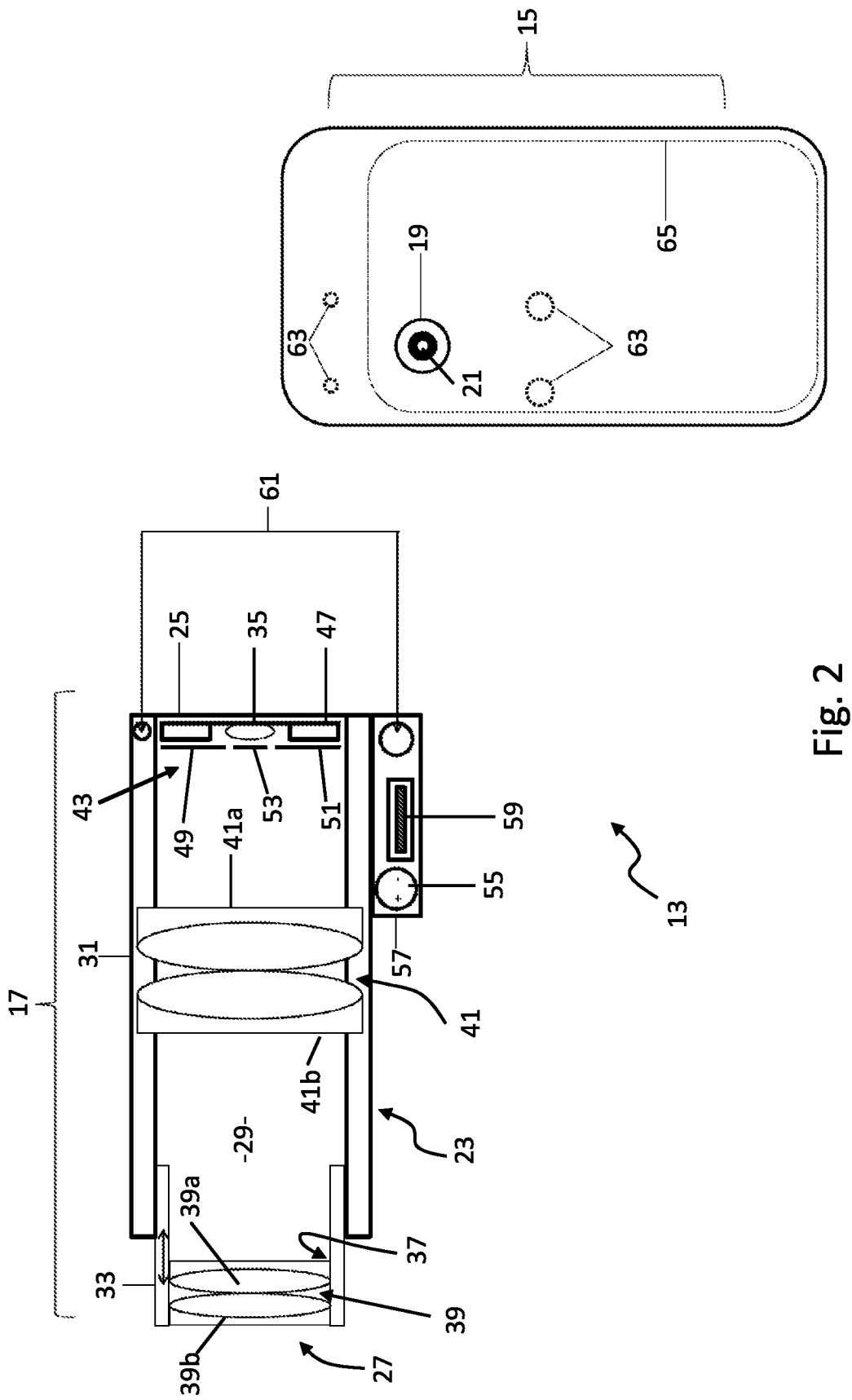
FIG. 2 shows a schematic representation of an adaptor including attachment means and the adaptor's relationship with a smartphone and smartphone cover.

Referring to FIG. 2, there is a shown a system 13 for fundus photography comprising a smartphone 15 and an adaptor 17 for attachment to and use with the smartphone 15 to enable the smartphone 15 to capture images of the fundus of a human eye 1.

The smartphone 15 comprises an image capture system having a camera aperture 19, a lens 21 and an image sensor (not shown) in the form of a CMOS chip which is configured to receive light waves from the smartphone exterior via the camera aperture and lens 21, and convert the received light waves into electrical signals for further processing by the smartphone 15. The smartphone 15 further comprises a light source (not shown) for illuminating objects for image acquisition, a processor (not shown), a memory (not shown), and a display screen (not shown) for interacting with the smartphone 15 and viewing images or video footage captured by the image capture system. Whilst a smartphone 15 is described in the present embodiment, it will be apparent to the person skilled in the art that other mobile image capture devices such as tablet computers may be used with the adaptor for enabling the image capture devices to capture images of the fundus of the human eye.

The adaptor 17 comprises a housing 23 having a first end 25 for attachment to the smartphone 15 and a second end 27 remote from the first end 25 and configured to be directed toward the pupil 5 of a human eye 1 for receipt of light waves from inside the human eye 1. The housing defines a passage or tube 29 along which light waves may travel between the first end 25 and the second end 27. The tube 29 comprises a base tube portion 31 extending from the first end 25 of the housing 23 and a tube extension 33 portion arranged at the second end 27 of the housing 23 and slidably engaged with the base tube portion 31 so that the tube extension portion 33 can move relative to the base tube portion 31. The base tube portion 31 comprises a base aperture 35 at the first end 25 of the housing 23 and the tube extension portion 33 defines a tube extension aperture 37 at the second end 27 of the housing 23 to enable light waves to enter and exit the tube 29 and travel between the first end 25 and second end 27 of the housing 23.

The tube extension portion 33 comprises an objective lens arrangement 39 configured to redirect light entering and exiting the housing 23 at the second end 27 via the tube extension aperture 37. The base tube portion 31 comprises a secondary lens arrangement 41 configured to redirect light waves travelling along the tube 29. In the embodiment depicted, the objective lens 39 is a relatively high-powered compound condensing lens and the secondary lens 41 is also a compound condensing lens of a relatively lower converging power than the objective lens 39. Both the objective condensing lens 39 and the secondary condensing lens 41 comprise a pair of positive achromatic doublet lenses 39a, 39b, 41a, 41b and are arranged in parallel such that they share a common optic axis which is substantially aligned with the centre of the base aperture 35 and tube extension aperture 37. The objective lens 39 has a front focal point OFP and a back focal point OBP which are equidistant either side of the objective lens 39. Likewise, the secondary lens has a front focal point SFP and back focal point SBP which are equidistant either side of the secondary lens 41. This optical system is chosen because it can capture a wide area of the retina of an eye with minimal distortion and aberration. However, it will be apparent to the person skilled in the art that other optical systems comprising condensing lenses that have sufficient converging power but with minimal aberration are possible.

The doublet lenses 39a, 39b of the objective lens 39 are substantially identical to one another and arranged such that the more convex sides of the doublet lenses 39a, 39b face one another. Likewise, the doublet lenses 41a, 41b of the secondary lens 41 are substantially identical to one another and arranged such that their more convex sides face one another. The diameter of the secondary lens 41 is chosen to be greater than or equal to the diameter of the objective lens 39. In the embodiment depicted, the doublet lenses 39a, 39b of the objective lens 39 have a diameter of approximately 20 mm and an effective focal length of approximately 10 mm on each side respectively of the objective lens arrangement. The doublet lenses 41a, 41b of the secondary lens 41 have a diameter of approximately 25 mm and an effective focal length of approximately 30 mm on each side respectively of the secondary lens 41.

The secondary lens 41 is fixed in place within the base tube portion 31 at a position spaced from the first end by approximately 30 mm so that the back focal point substantially falls within a region between with the plane of the base aperture 35 and the plane of the camera aperture 19 when the adaptor 17 is attached to the smartphone 15. The objective lens 39 is fixed in place within the tube extension 33 portion and movable with the tube extension portion 33 relative to the base tube portion 31 and, hence, the secondary lens 41. Thus, the position of the objective lens 39 can be adjusted such that the back focal point OBP of the objective lens 39 substantially coincides with the front focal point SFP of the secondary lens 41.

Figure 3:
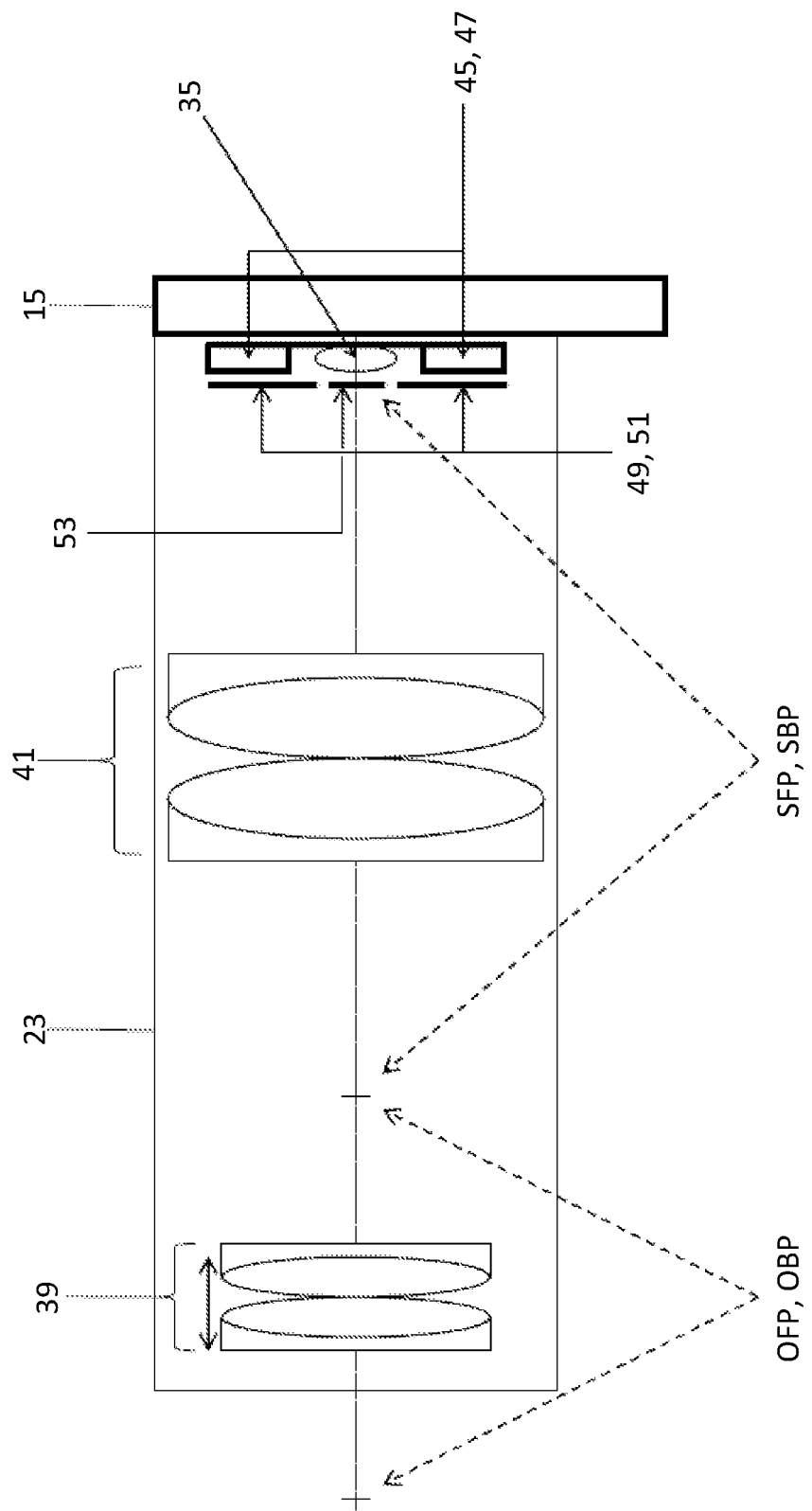
FIG. 3 shows a schematic cross section of part of the adaptor shown in FIG. 2 in combination with a smartphone when viewed from above.
Figure 4:
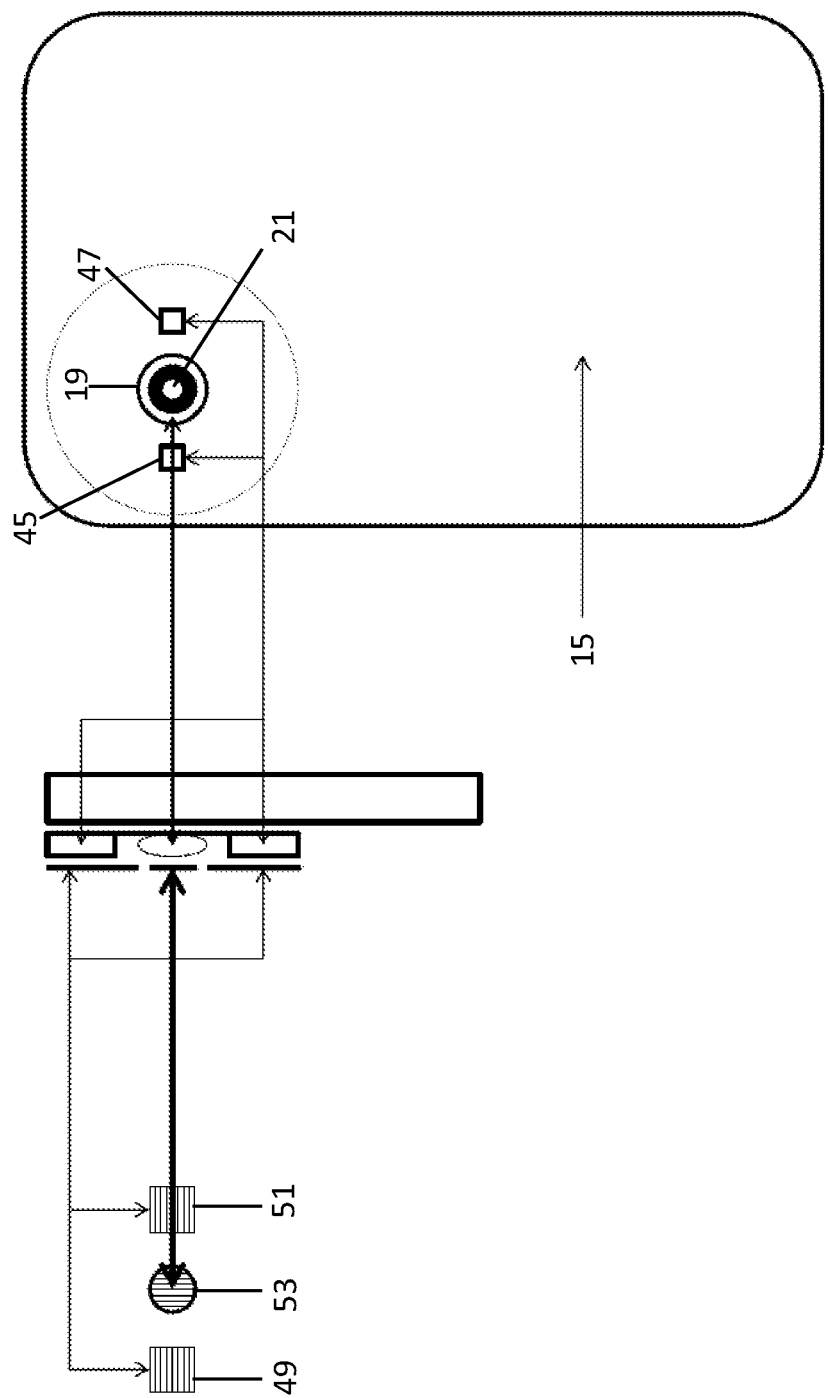
FIG. 4 shows part of the adaptor shown in FIG. 2 and its intended positional relationship with the lens of a smartphone.

Referring to FIG. 2 in combination with FIGS. 3 and 4, the adaptor 17 further comprises a light module 43 comprising a pair of light emitting diodes (LEDs) 45, 47 arranged either side of the base aperture 35 and configured to direct light waves into the tube 29 toward the secondary lens 41. The distance between the inner edges of the LEDs 45, 47 represents the inner border of the light emitted by the light module 43 and the distance between the outer edges of the LEDs 45, 47 represents the outer border of the LEDs 45, 47. The base aperture 35 is sized and positioned such that when the adaptor 17 is correctly attached to and aligned with the smartphone 15 the base aperture 35 is aligned with and surrounds the camera aperture 19 so that light waves can enter the camera aperture 19 from the adaptor 17 exterior via the tube 29.

A linear polarizer 49, 51 is positioned in front of each LED 45, 47 such that only light waves of a particular polarization emitted by each LED 45, 47 are permitted to enter the tube 29 so as to reduce unwanted reflections from smooth surfaces. An analyser 53 comprising a plate linear polarizer is positioned across the base aperture 35 so that only light waves of a particular polarization are permitted to enter the camera aperture 19 from the tube 29. The axis of polarization of the LED polarizers 49, 51 is separated from the axis of polarization of the analyser by a 90 degree angle so that the polarized light from the LEDs 45, 47 is filtered out by the analyser 53 and does not enter the camera aperture 19 and interfere with the quality of the image received by the smartphone 15 via the adaptor 17.

Whilst a pair of LEDs 45, 47 are shown in the present embodiment, it will be apparent to the person skilled in the art that other combinations are possible with respect to the number of LEDs, and the colour temperature, wavelength, and intensity of the light, all of which may be varied according to imaging conditions and requirements. For example, the adaptor may comprise only a single LED or a ring of LEDs encircling the base aperture. In addition, whilst linear polarizers are used in the present embodiment, any suitable type of polarizer may be used provided that the polarization orientation of the analyser is different from the polarization orientation of the LED polarizers so that light from the LEDs that might be reflected inside the tube is filtered out and does not interfere with the image received by the smartphone camera. For example, a circular polarizing filter may be used in place of one or more of the linear polarizers.

The adaptor 17 further comprises a power source 55 in the form of a cell battery contained within a compartment 57 of the housing 23 separate from the tube 29. The cell battery 55 is electrically connected to the light module 43 to provide power to the light module 43 when required to be operational. Activation of the light module 43 by a user is facilitated by a switch 59 arranged on the housing 23 and operable between an "on" position in which the LEDs 45, 47 are powered to emit light and an "off" position in which no power is provided to the LEDs 45, 47. In an alternative embodiment, the adaptor 17 may be configured to draw power from the smartphone battery either through direct electrical contact or wireless power transfer.

The adaptor 17 further comprises a series of magnets 61 spaced apart about the first end 25 of the housing 23 and configured to be attracted to correspondingly positioned magnets 63 of a smartphone case 65. The smartphone case 65 is sized and configured to be connected to the smartphone 15 to protect the smartphone 15 and to permit the adaptor 17 to be accurately positioned relative to the camera aperture 19 of the smartphone 15. The magnets 63 of the smartphone case 65 and the corresponding magnets 61 of the adaptor 17 are positioned such that when the adaptor 17 is attached to the combined smartphone 15 and smartphone case 65, the base aperture 35 is aligned with and surrounds the camera aperture 19 such that the optic axis of the objective lens 39 and secondary lens 41 is substantially aligned with the optic axis of the lens 21 of the smartphone 15. It will be apparent to those skilled in the art that other suitable means of attachment are possible such as sliding engagement, fasteners, and clips.

Figure 5:
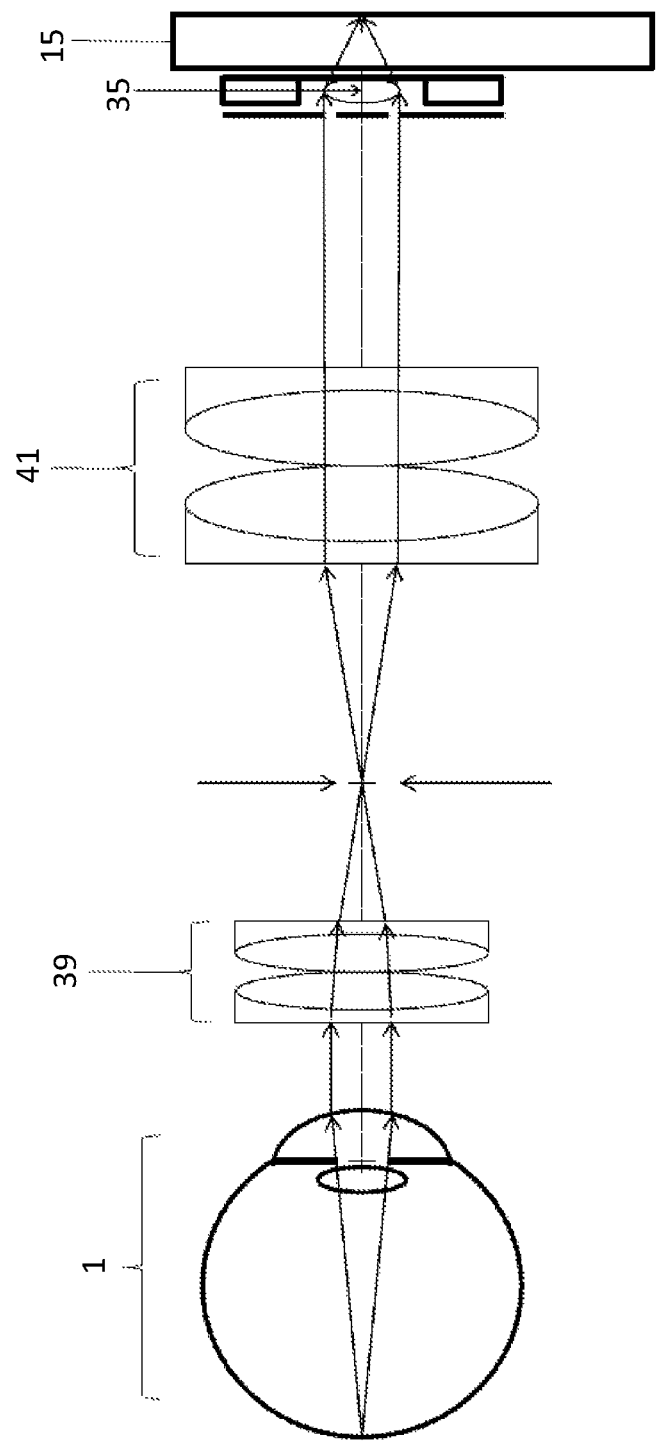
FIG. 5 shows a ray diagram of a viewing pathway with respect to image position in relation to parts of the adaptor shown in FIG. 2 and the eye.

With reference to FIG. 5, the adaptor 17 is configured to re-direct light waves from inside the eye 1 along a first pathway and into the camera aperture 19 of the smartphone 15. This pathway from the eye to the camera may be referred to as a viewing pathway. When the optic axis of the adaptor 17 is aligned with the optic axis of the lens 7 of an eye 1, a cone of light waves emanating from a point of the retina 9 passes through the pupil 5 of the eye 1 and is collimated by the cornea 3 of the eye 1 so that it is directed toward the objective lens 39 via the second end 27 of the adaptor 17. The objective lens 39 serves to focus the light waves on a back focal point OBP, thereby forming a real image at an intermediate image plane between the objective lens 39 and the secondary lens 41. When the position of the objective lens 39 relative to the secondary lens 41 is such that the back focal point OBP of the objective lens 39 substantially coincides with the front focal point SFP of the secondary lens 41, the light waves related to the real image are collimated by the secondary lens 41 to produce parallel light waves that are directed toward the camera aperture 19 through the base aperture 35. The smartphone lens 21 focusses the parallel light waves onto the smartphone sensor for image capture. Since the light waves entering the smartphone camera aperture are parallel, the smartphone perceives the image of the retina at infinity.

Figure 6:
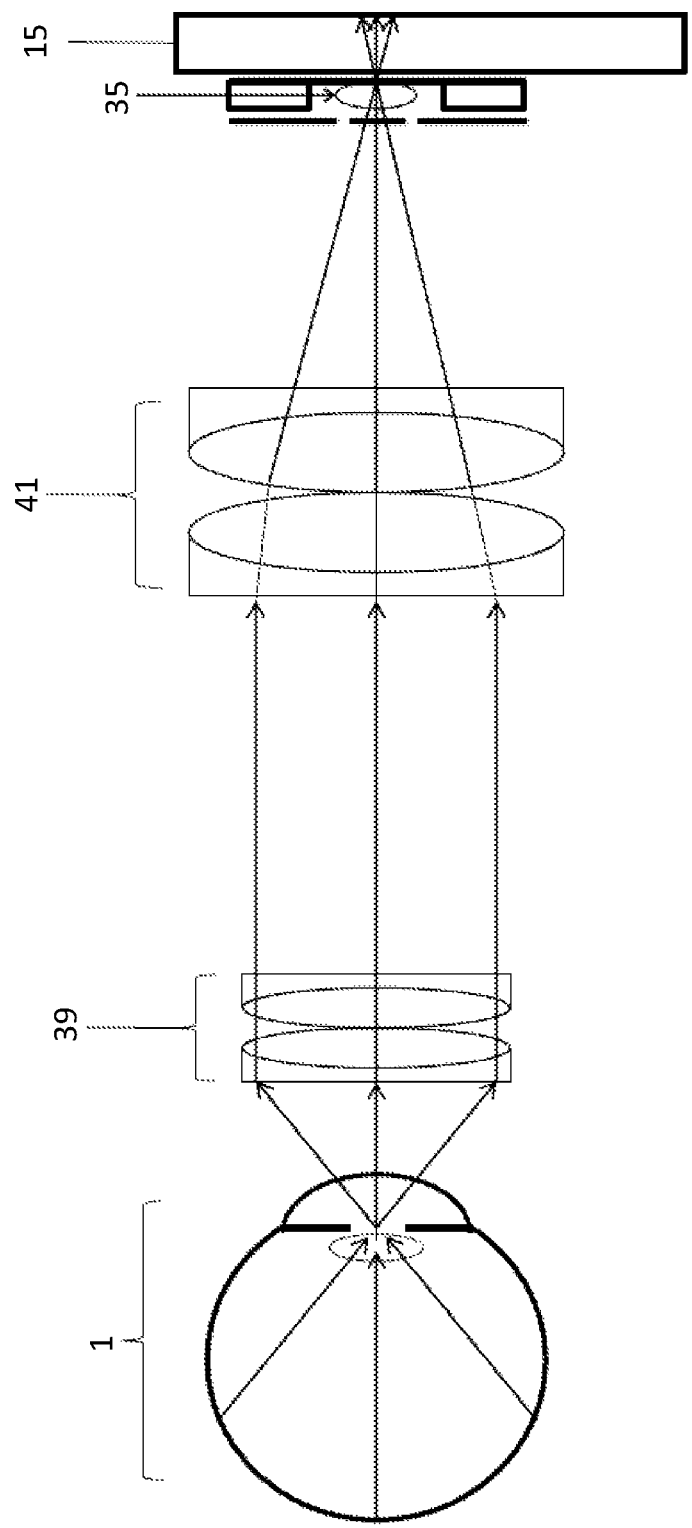
FIG. 6 shows a ray diagram of a viewing pathway with respect to field of view in relation to parts of the adaptor shown in FIG. 2 and the eye.

Referring to FIG. 6, the adaptor 17 is capable of redirecting light waves from a large area of the retina toward the camera aperture 19 so that a large field of view (a large circle of the retina 9) is visible through the adaptor 17. Only the chief light waves from the retina 19 are depicted for illustrative purposes. The true field of view achievable by the adaptor 17 is determined primarily by the numerical aperture of the objective lens as defined by the equation Numerical Aperture=n Sin $\theta$ (where n is the refractive index of the imaging medium, which is 1.0 for air). Since a higher numerical aperture translates into a greater true field of view, the numerical aperture should be as large as possible, for example 1.0, to enable the adaptor 17 to achieve a large true field of view. The chief light waves entering the adaptor 17 from the eye 1 are collimated by the objective lens 39, thereby sending parallel light waves towards the secondary lens 41, which focusses the collimated light waves at the secondary lens' back focal point SBP. Since the secondary lens 41 is spaced from the back aperture 35 such that the back focal point coincides with the back aperture 35 in proximity to the camera aperture 19, all of the chief light waves are received by the smartphone camera and fall upon the sensor. Ideally, the size of the image falling upon the sensor should be equal to the sensor area to achieve maximum image resolution.

Since the secondary lens 41 diameter is greater than or equal to the objective lens 39 diameter, all of the light waves within the light cone defined by the chief light waves are received by the smartphone 15. Otherwise, if the secondary lens diameter is less than the objective lens diameter, light waves from the peripheral part of the retina may be lost at the periphery of the secondary lens 41 and vignetting at the edges of the image may result.

The field of view of the optical system can be calculated as followed:

For the true field of view (TFOV), $$\tan(TFOV/2) = \text{diameter of objective lens}/(2 \times \text{focal length of objective lens}) \quad (1)$$

For the apparent field of view (AFOV) at the smartphone camera:

$$\tan(AFOV/2) = \text{diameter of objective lens}/(2 \times \text{focal length of secondary lens}) \quad (2)$$

Thus, in the embodiment depicted, the TFOV and the AFOV are calculated as follows:

The actual field of view of the retina=$2 \times \tan^{-1}(20/20)$=90 degrees

The apparent field of view at the camera side=$2 \times \tan^{-1}(20/60)$=36.9 degrees Therefore, the retinal image size visible on the smartphone display will appear as 36.9 degrees of arc.

Figure 7:
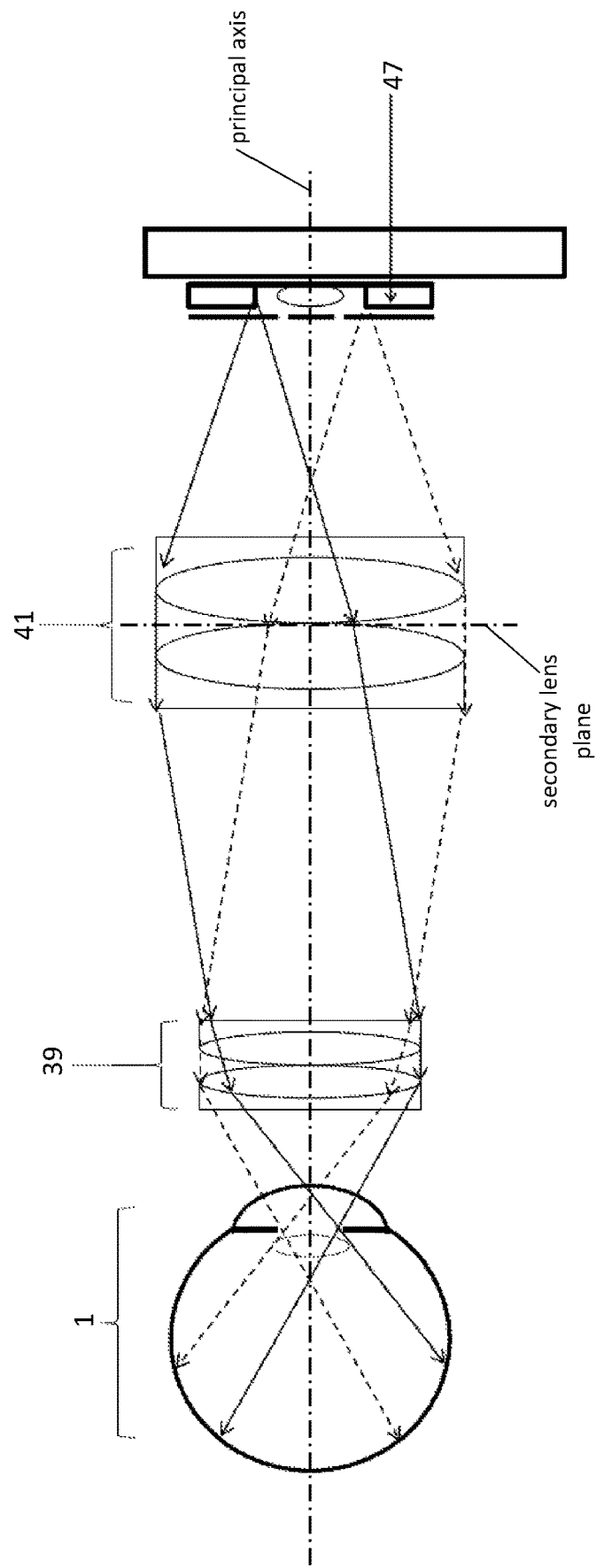
FIG. 7 shows a ray diagram of illumination pathways in relation to parts of the adaptor shown in FIG. 2 and the eye.

With reference to FIG. 7, the adaptor 17 is configured to direct light from the light module 43 along a second pathway which is different from the first pathway. This second pathway from the light module 43 to the eye 1 may be referred to as an illumination pathway. Light waves from the LEDs 45, 47 of the light module 43 pass through the polarizers 49, 51 and are directed to the secondary lens 41 which redirects the light waves toward the objective lens 39. For illustrative purposes, the light pathway of light waves emanating from the inner edges of the LEDs 45, 47 are shown. As can be seen, a cone of light waves emanating from an inner edge of one LED 45 is redirected by the secondary lens 41 such that the light waves proceed as a parallel beam of light at an oblique angle toward the objective lens 39. This oblique angle is calculated based upon the distance between the inner edge of an LED 45 and the centre of the base aperture, and the distance from the LED 45 to the secondary lens plane as measured along a line parallel to the principal axis. Likewise, the cone of light emanating from the inner edge of the other LED 47 is redirected as a parallel beam of light at an oblique angle toward the objective lens 39. The oblique angle is determined by the equation:

$$\theta_{oblique} = \tan^{-1}(\text{distance from inner edge to centre of base aperture}/\text{distance from LED to secondary lens plane}) \quad (3)$$

When the adaptor 17 is appropriately positioned relative to an eye 1 such that the centre of the pupil 5 is aligned with the principal axis of the adaptor 17 and the pupil 5 is at a working distance from the end of the adaptor 17, both beams of light are focussed by the objective lens 39 toward respective points on the pupil plane of the eye 1 but offset from the principal axis. The light module 43, secondary lens 41, and objective lens 39 are together configured such that each beam from the light module is focussed at a point in the vicinity of the pupil edge, away from the pupil centre. Thus, the beams diverge upon passing through the pupil 5 to cover and, hence, illuminate a wide area of the retina 9.

Figure 8:
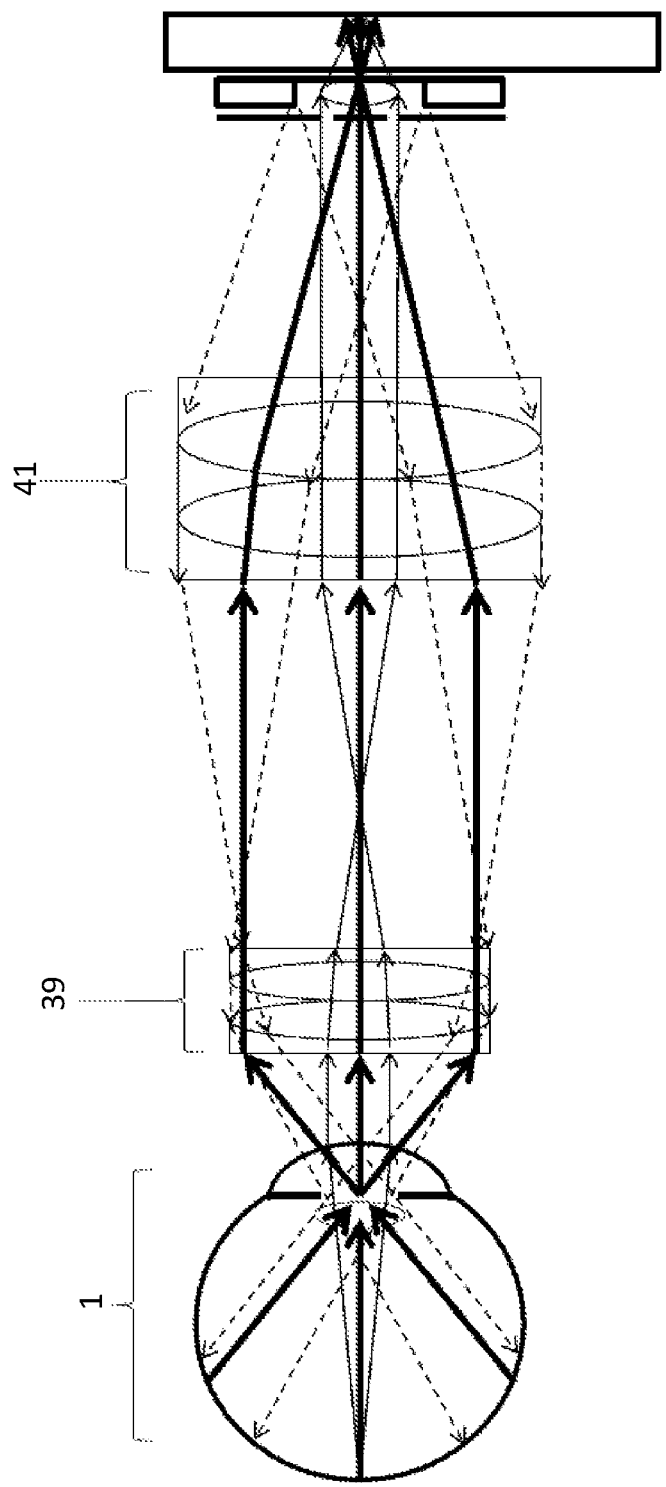
FIG. 8 shows a complete ray diagram of illumination pathways and a viewing pathway in relation to parts of the adaptor shown in FIG. 2 and the eye.

With reference to FIG. 8, a complete ray diagram is shown comprising the illumination pathways (depicted in dotted lines) of the cones of light emanating from the inner edges of the two LEDs 45, 47, the chief rays of light (depicted in bold lines) reflected from the retina 9 toward the adaptor 17, and the example marginal rays (depicted in thin solid lines) reflected from a central point of the retina 9 toward the adaptor 17. As can be seen, the illumination pathways are different from the viewing pathways of the chief rays and marginal rays such that the light travelling along the illumination pathway enters the eye at a peripheral region of the pupil 5 that does not interfere with the region of the viewing pathway exiting the pupil 5.

Figure 9:
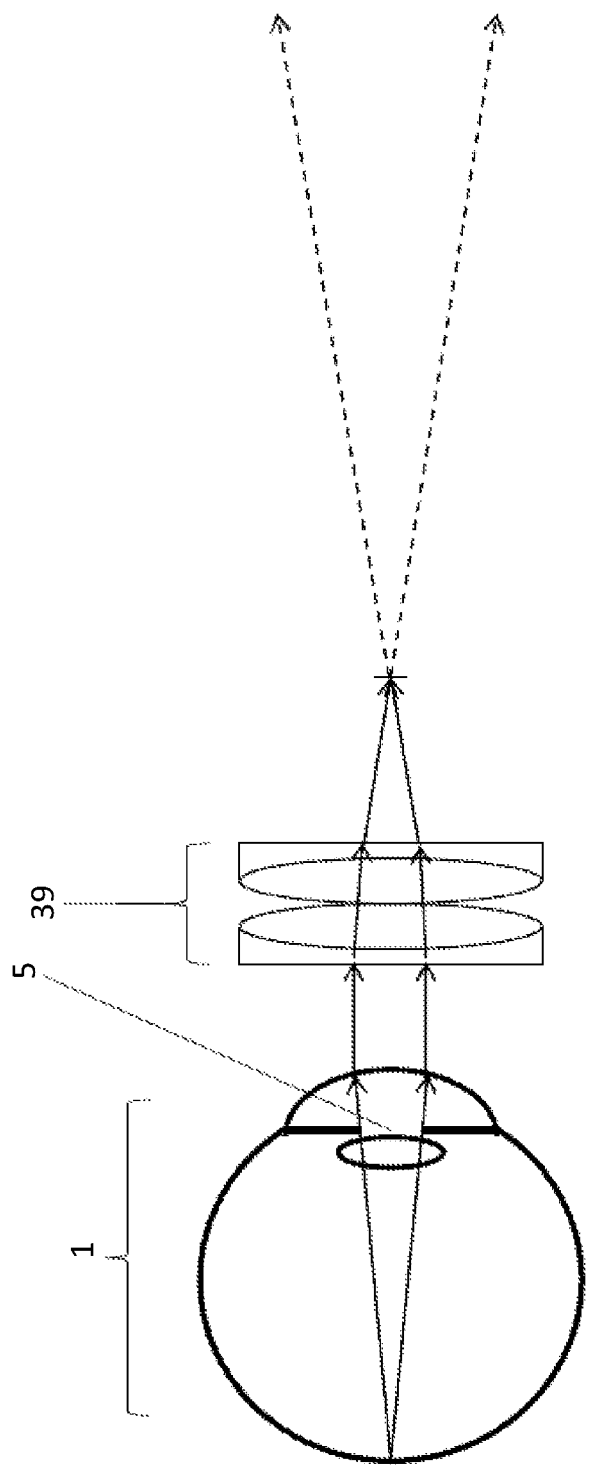
FIG. 9 shows a ray diagram indicating the relationship between an aperture stop and a part of the adaptor shown in FIG. 2.
Figure 10:
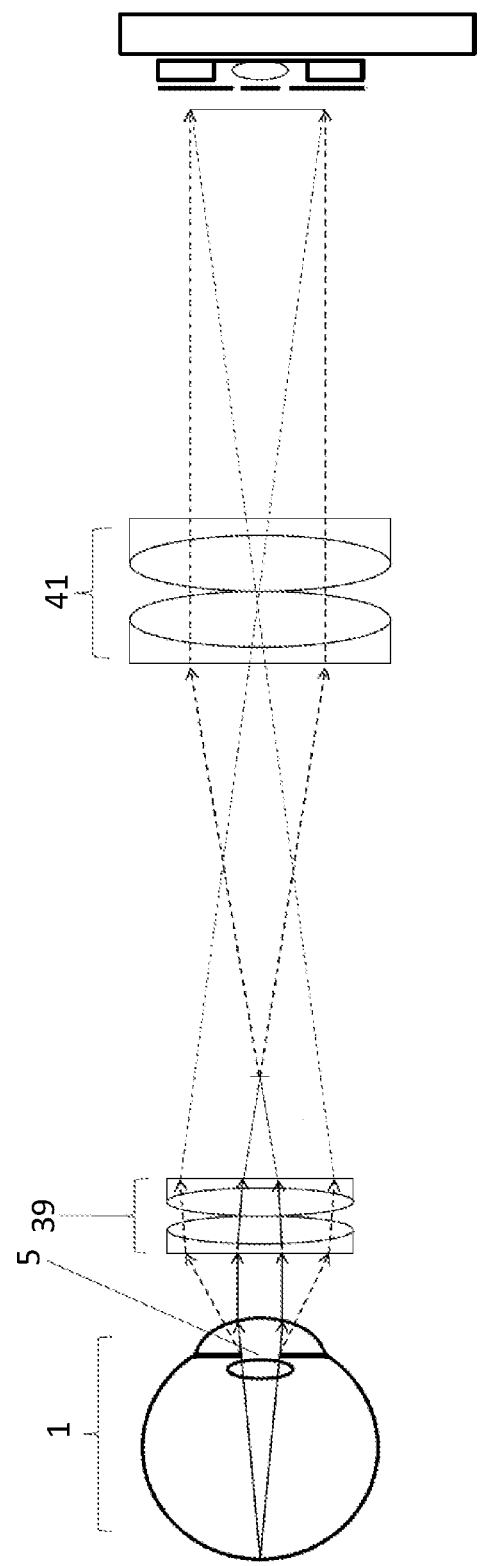
FIG. 10 shows a ray diagram demonstrating the relationship between pupil diameter and the viewing pathway.

When constructing the adaptor 17 and internal optical system, the aperture stop formed by the pupil 5 defined by the iris of the eye must be taken into account as this impacts upon the position of the light source relative to the back aperture 35 and camera aperture 19. The pupil 5 of an average human is adjustable in diameter between a minimum diameter of approximately 2 mm and a maximum diameter of approximately 8 mm. With reference to FIG. 9 which depicts a simplified system comprising only an objective lens 39 for refocussing light from inside the eye 1, the image of the pupil 5 is projected to infinity as shown by the divergent dotted lines. With the introduction of the secondary lens 41 into the optical system, as shown in FIG. 10, the image of the pupil 5 is re-focussed at the back focal point SBP of the secondary lens 41. The magnification of the image of the pupil is dependent on the respective focal lengths of the objective and secondary lenses and is given by the equation:

$$M = \text{focal length of secondary lens}/\text{focal length of objective lens}. \quad (4)$$

In the present embodiment, assuming the average pupil diameter of a human eye (after being subject to dilating eye drops) is 8 mm, and with an effective focal length of the objective lens of 10 mm, and an effective focal length of the secondary lens of 30 mm, the diameter of the magnified image of the pupil is 8×30/10=24 mm. Thus, provided the light source can be configured to emit light from a position within an area having a diameter of 24 mm centred about the camera aperture 19, simultaneous illumination and viewing of the fundus of the eye 1 through the pupil 5 is possible using an adaptor 17 according to the present embodiment. Since the aperture stop of modern smartphone cameras is around 2-3 mm, and since the size of modern LED units can be as little as 1 mm across, the camera aperture and light source can be combined together within a small area less than 24 mm across without much difficulty. It will be apparent to the skilled person that one or more LED units could be positioned outside of this area but combined with one or more fibre optic cables to direct light into the tube 29 from a position within this 24 mm diameter.

Figure 11:
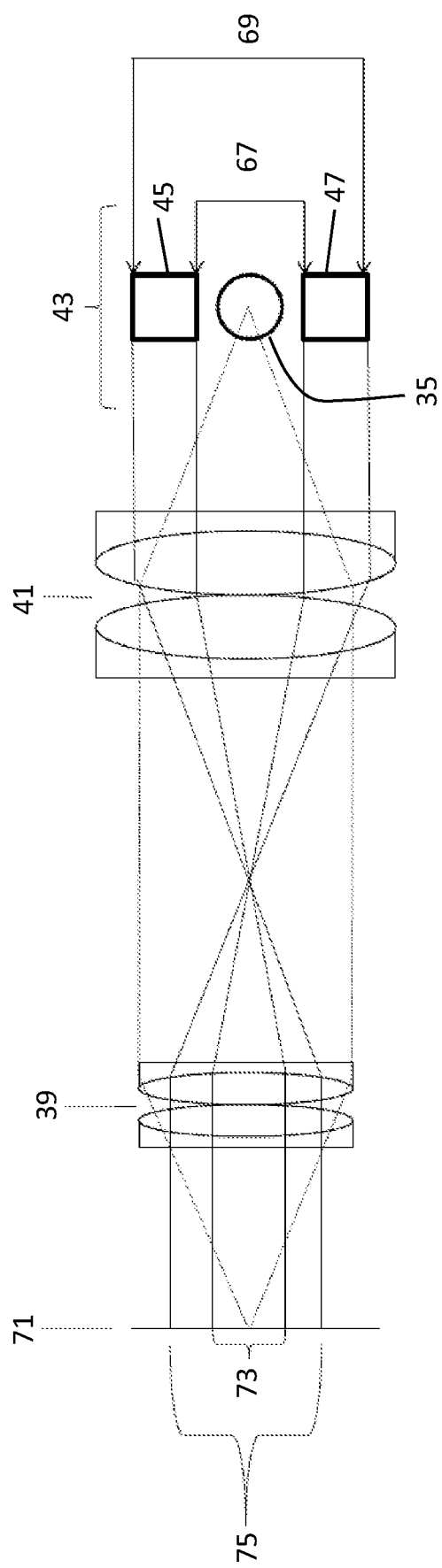
FIG. 11 shows a ray diagram demonstrating the relationship between pupil size and illumination pathway in relation to parts of the adaptor shown in FIG. 2.

The impact of pupil size on design considerations for the adaptor is further illustrated with reference to FIG. 11 which depicts the minimum and optimal illumination pathways of the adaptor 17. As can be seen, the illumination pathways of light emanating from the inner edges and outer edges, respectively, of the LEDs 45, 47 of the light module is shown. Light waves from both the inner edges 67 and outer edges 69 of the LEDs 45, 47 are projected through the secondary lens 41 and objective lens 39 and redirected to form parallel rays directed toward the pupil plane 71 of the eye 1. The image 73 formed by the inner border defines the minimal pupil diameter required for permitting entry of the light waves for illumination of the eye interior. The image formed by the outer border 75 defines the optimal pupil size such that all light from the LEDs 45, 47 can enter the eye interior. Thus, for optimal illumination and imaging performance, the pupil should be dilated to its maximum extent. However, as can be seen, even with a small pupil size, provided the pupil is greater in diameter than the diameter of the image 73 formed by the inner edges 67 of the LEDs 45, 47, illumination of the eye interior and imaging of the fundus is still possible.

The geometrical relationship between the position of the light source relative to the camera aperture and pupil size is given by:

$$\text{optimal pupil size/focal length of objective lens} = \text{distance between outer edges of the LEDs/focal length of secondary lens} \quad (5)$$

$$\text{minimal pupil size/focal length of objective lens} = \text{distance between inner edges of the LEDs/focal length of secondary lens} \quad (6)$$

Thus, for the described embodiment, assuming a lowest possible pupil diameter of 2 mm and a maximum possible pupil diameter of 8 mm, the minimum and maximum distances between the inner and outer edges, respectively, of the LEDs 45, 47 are as follows:

$$\text{minimum distance between inner edges} = (2*30)/10 = 6 \text{ mm}$$

$$\text{maximum distance between outer edges} = (8*30)/10 = 24 \text{ mm}$$

Therefore, in the embodiment depicted, the light source is arranged to direct light into the tube 29 toward the secondary lens 41 from a point or region positioned in an area between a maximum diameter of 24 mm and a minimum diameter of 6 mm centred on the back aperture 35 (i.e. between 12 mm and 3 mm from the back aperture centre) and, hence, camera aperture 19 when aligned along the principal axis. Thus, illumination light will be focussed by the adaptor 17 at a point in space in front of the adaptor 17 at which an appropriately positioned eye 1 will receive illumination light into the eye interior via the pupil. Provided the eye 1 is positioned such that the optical axis of the pupil 5 is aligned with the principal axis, the illumination light is focussed at a position offset from the principal axis at or about the pupil plane at a peripheral region of the pupil 5.

Figure 12:
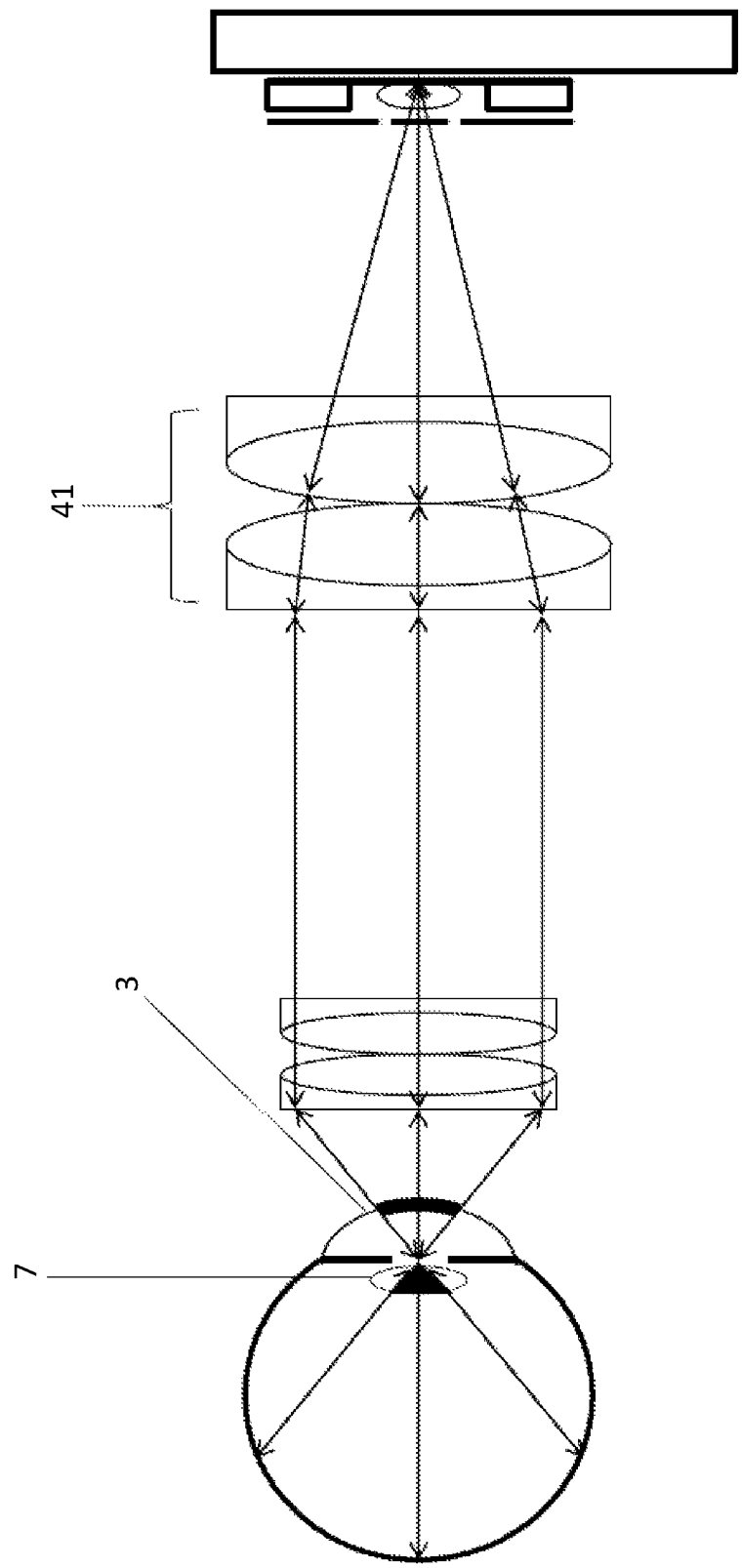
FIG. 12 shows a ray diagram demonstrating the relationship between the illumination pathway and the viewing pathway when the aperture of a camera and a light source are arranged at the same optical position.

Focussing illumination light at the peripheral region of the pupil plane is particularly important when attempting to optimise fundus photography as it reduces backscattering of light caused by the patient's cornea 3 and lens 7. Referring to FIG. 12, if the back aperture 35 and light source are placed at the same optical position, light waves from the light source will be directed by the adaptor 17 along an illumination pathway that passes through the same region of the cornea 3 and lens 7 as light waves travelling along the viewing pathway. Because the cornea 3 and lens 7 are optically dense media that produce a relatively strong back-scattering effect, the viewing pathway is severely contaminated by such back-scattering, thereby rendering the image of the retina virtually un-viewable.

Figure 13:
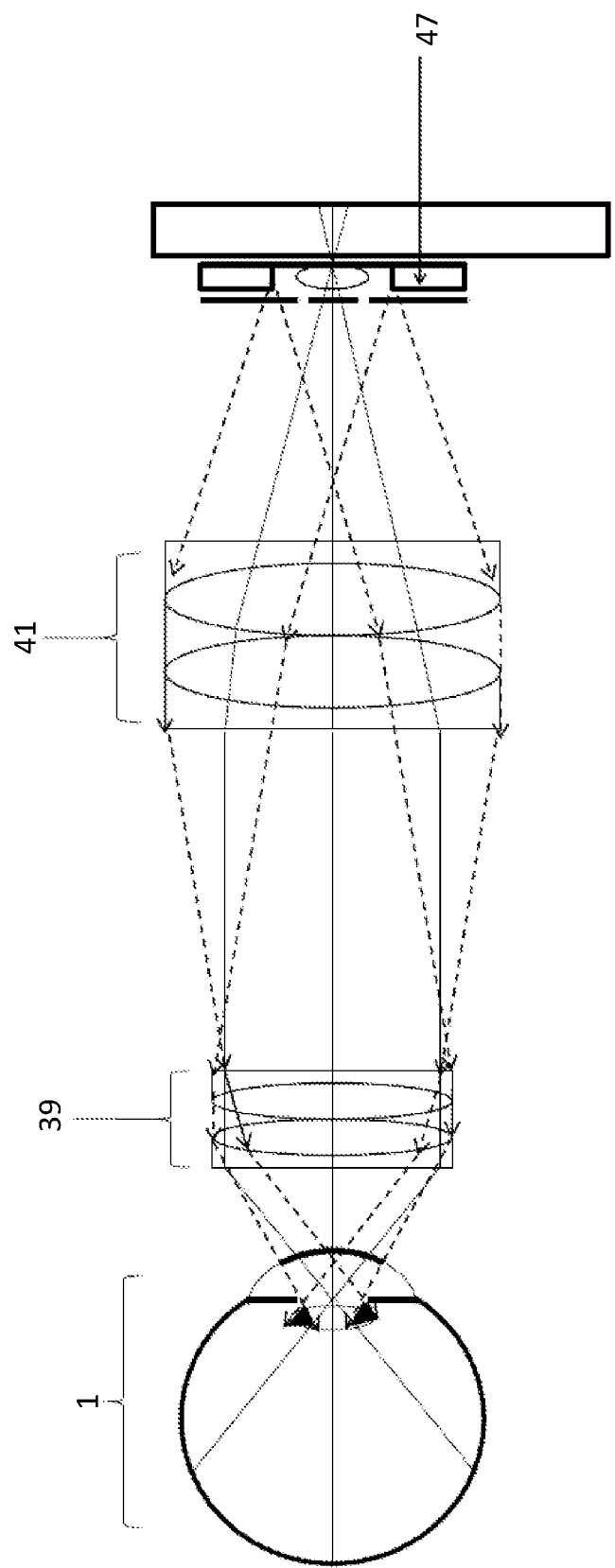
FIG. 13 shows a ray diagram demonstrating the relationship between the illumination pathway and the viewing pathway when the optical position of the light source is offset from the optical position of the lens.

The adaptor 17 according to the present invention has therefore been configured such that, when the eye 1 is appropriately positioned relative to the adaptor and smartphone system, the illumination pathway and the viewing pathway mainly intersect at the retina 9 rather than the central region of the cornea 3 and lens 7, thereby producing a relatively glare-free image of the retina 9. With reference to FIG. 13, this is achieved by positioning the LEDs 45, 47 para-axially relative to the back aperture 35 and substantially coplanar with the back aperture 35 or camera aperture 19 such that the whole illumination beams of the LEDs are shifted obliquely. This ensures that the images of the LEDs 45, 47 are focused at the edge of the pupil 5 thereby avoiding crossing of the illumination pathways with the viewing pathways at the lens 3 and pupil plane 71. At the corneal plane, crossing of the illumination pathway and viewing pathway is unavoidable but manageable since the region of crossing of the pathways is dispersed across a wider area. As a result, the back-scattering effect due to illumination light at the central cornea is relatively mild and, thus, the image of the retina that is obtainable is of acceptable quality and, advantageously, may have a wide field of view.

Whilst it is preferable for the light source 45, 47 to be coplanar with the back aperture 35 or camera aperture 19, or somewhere there between, the adaptor 17 will still work relatively effectively if the light source is deviated axially (along the principal axis) slightly such that the final location of the image of light source 45, 47 will also be deviated slightly axially, e.g. slightly beyond or before the pupil plane. However, an axial deviation of the light source of more than a few millimetres will result in a corresponding deviation of the image of the light source relative to the pupil 5 of the eye 1, e.g. into the middle of eyeball, such that only a narrow field of retina illumination is achievable, thereby limiting the effectiveness of the adaptor 17 and the field of view that can be captured by the system.

Figure 15:
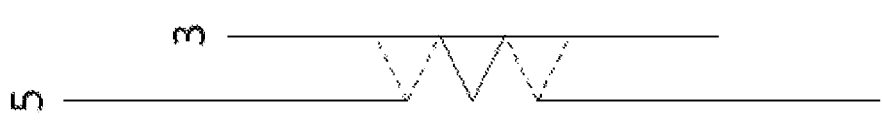
FIG. 15 shows a schematic representation of the anterior chamber between the pupil and the cornea and the relationship between light travelling along an illumination pathway and light travelling along a viewing pathway through the anterior chamber.

It is possible to modify the adaptor 17 such that the central part of the cornea occupied by the viewing pathway is absolutely uncrossed and devoid of illumination light so that the illumination light does not cause backscattering that might interfere with the captured image of the retina 9. This might be done by positioning a physical aperture (not shown) within the tube 29 along the illumination pathway between the secondary lens 41 and the objective lens 39 such that light waves that would otherwise cross the central part of the cornea are blocked. Uncrossing of the illumination pathway and the viewing pathway is depicted in FIG. 15 which shows the cone of illumination light from the two LEDs in dotted lines entering the anterior chamber between the cornea 3 and the pupil 5 and focussing on the pupil plane at a periphery of the pupil 5 offset from the pupil centre. Light waves exiting the eye via the pupil along the viewing pathway are depicted in solid lines and remain uncrossed with the illumination pathway through the anterior chamber. However, in this case, the area of the retina that can be simultaneously illuminated and viewed will be smaller because the physical aperture blocking the incoming illumination light waves also has the effect of blocking light waves from the eye interior travelling along the viewing pathway, thereby limiting the maximum field of view. The maximal field of view in this arrangement is given by the equation:

$$\theta_{viewing} = 2*\tan^{-1}(\text{pupil diameter}/(4*\text{anterior chamber depth})) \quad (7)$$

For an assumed maximal pupil diameter of 8 mm and a typical anterior chamber depth of 4 mm, the maximum viewing angle attainable for a completely uncrossed arrangement is 53.1 degrees. Therefore, whilst backscattering can be eliminated with an appropriately positioned physical aperture within the adaptor 17, the maximum field of view is significantly less than the maximum field of view of 90 degrees attainable with the above described embodiment without a physical aperture.

Figure 14:
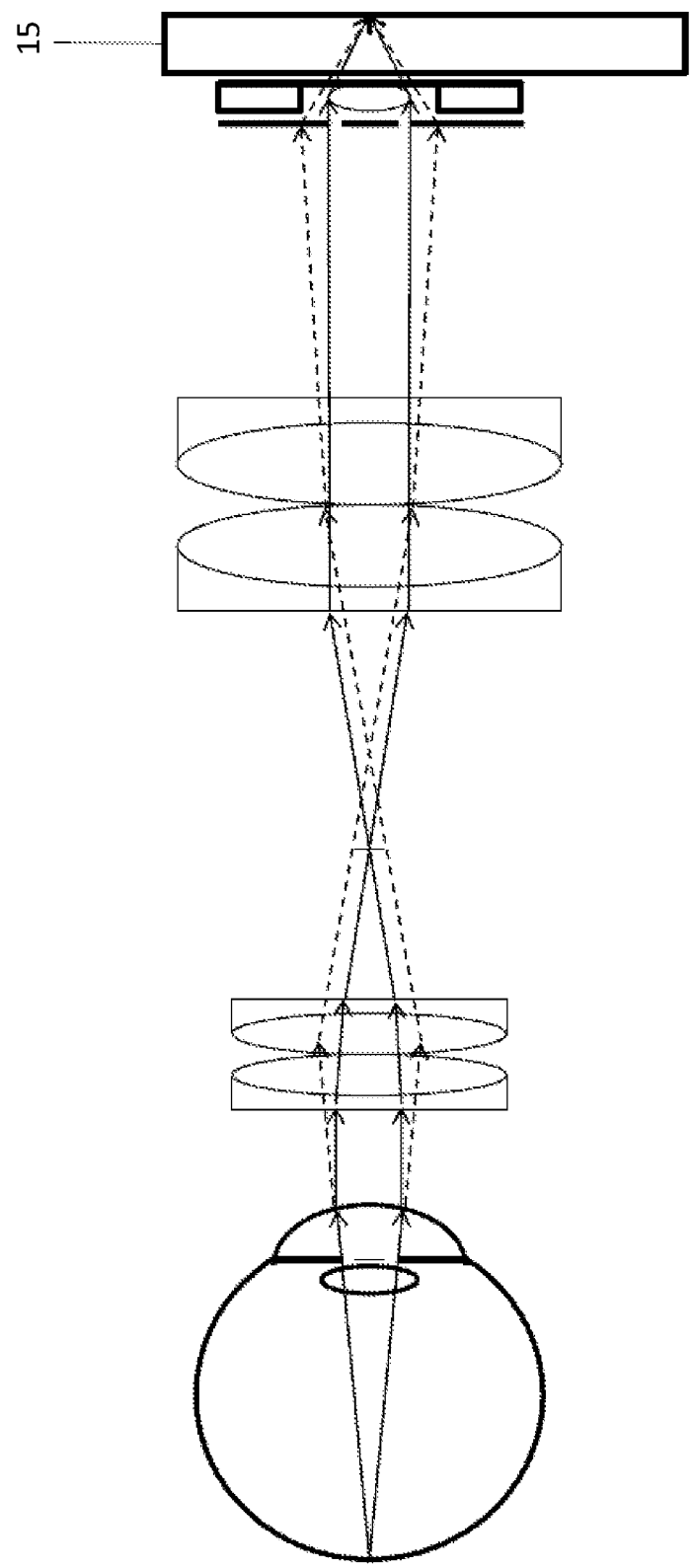
FIG. 14 shows a ray diagram comparing the image pathway of a normal sighted person with a far sighted person and demonstrating the focussing ability of a smartphone camera.

Since the objective lens 39 is movable relative to the secondary lens 41 such that the position of the back focal point OBP of the objective lens 39 can be adjusted, the adaptor 17 is capable of capturing fundus photographs in eyes with different refractive errors. With reference to FIG. 14, for a person with hypermetropia (i.e. far or long sighted), light waves from inside the eye through the pupil 5 are divergent such that the image of the retina 9 is focussed by the objective lens 39 further from the objective lens 39 and closer to the secondary lens 41 (as depicted by broken lines). Therefore, light waves of this image will also exit from the secondary lens 41 as divergent rays that are not directed as a parallel beam through the base aperture 35 and camera aperture 19, respectively. By adjusting the position of the objective lens 39 relative to the secondary lens 41, it is possible to position the intermediate plane of the real image such that it coincides with the front focal point SFP of the secondary lens 41 so that the light waves are focussed by the secondary lens 41 through the base aperture 35 and camera aperture 19 for focussed image capture.

Whilst the objective lens 39 in the present embodiment is movable relative to the secondary lens 41, due to advances in smartphone camera technology, for patients with refractive error, in certain circumstances it may not be necessary to move the objective lens 39 relative to the secondary lens 41 such that their respective front and back focal points coincide. This is because the smartphone camera auto focus can obtain a sharp image even when receiving unfocussed light waves via the adaptor 17. Whether or not the camera autofocus has the ability to account for refractive error of the human eye and produce a sharp image can be estimated by determining the location of the intermediate image focused by the objective lens 39 for given refractive errors as calculated using the thin lens equation:

$$1/\text{focal length} = 1/\text{object distance} + 1/\text{image distance} \quad (8)$$

The refractive error of the human eye is measured in dioptres, which is the reciprocal of the focal length of the eye lens 7 in metres. This number refers to the power of the lens, in dioptres, required to be placed in front of the eye in order to focus parallel rays of light onto a single spot on the retina 9. Normally, the refractive error of human eyes seldom exceeds the range from −20 dioptres (short sightedness) to +20 dioptres (long sightedness).

Figure 16:
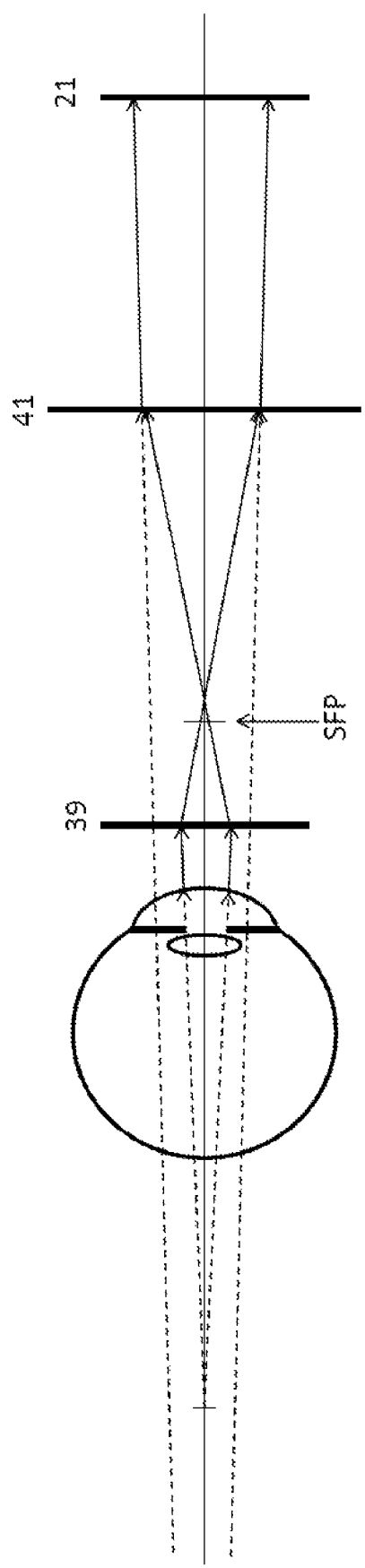
FIG. 16 shows a ray diagram demonstrating the effect of refractive error in the eye of a long sighted person relative to the optical system of the adaptor.

With further reference to FIG. 14 and also to FIG. 16, in the case of a person with hypermetropia that results in divergent light waves entering the smartphone camera lens 21, the smartphone 15 acts as if a real object is placed in front of the smartphone camera. FIG. 16 depicts a ray diagram for a patient at the extreme end of long sightedness with +20 dioptres of hypermetropia. For such a patient, light waves from a point on the retina 9 emerge from the eye 1 as if originating from an object/point located 50 mm behind the corneal plane. Assuming the cornea 3 is 4 mm in front of the pupil 5, when the objective lens 39 having a focal length of 10 mm is positioned such that the front focal point is at or about the pupil plane, the objective lens 39 is approximately 6 mm in front of the cornea 3. Thus, in this position, light reaching the objective lens 39 from a point on the retina 9 is equivalent to an object being situated 56 mm to the left of the objective lens 39.

Using the thin lens equation (1/10=1/56+1/image distance), the intermediate image of the retina 9 formed by the objective lens 39 is located 12.2 mm to the right of the objective lens 39. Thus, the intermediate image is formed approximately 2.2 mm to the right of the secondary lens front focal point SFP. This results in the light waves of the retina image remaining slightly diverged after passing through the secondary lens 41, thereby giving rise to the formation of a virtual image approximately 379 mm to the left of the secondary lens 41. Therefore, including the distance of approximately 30 mm from the secondary lens 41 to the camera lens 21, the smartphone camera perceives the image of the retina 9 as if it is located 409 mm from the lens 21. This perceived distance is easily within the autofocus capabilities of modern smartphones.

Figure 17:
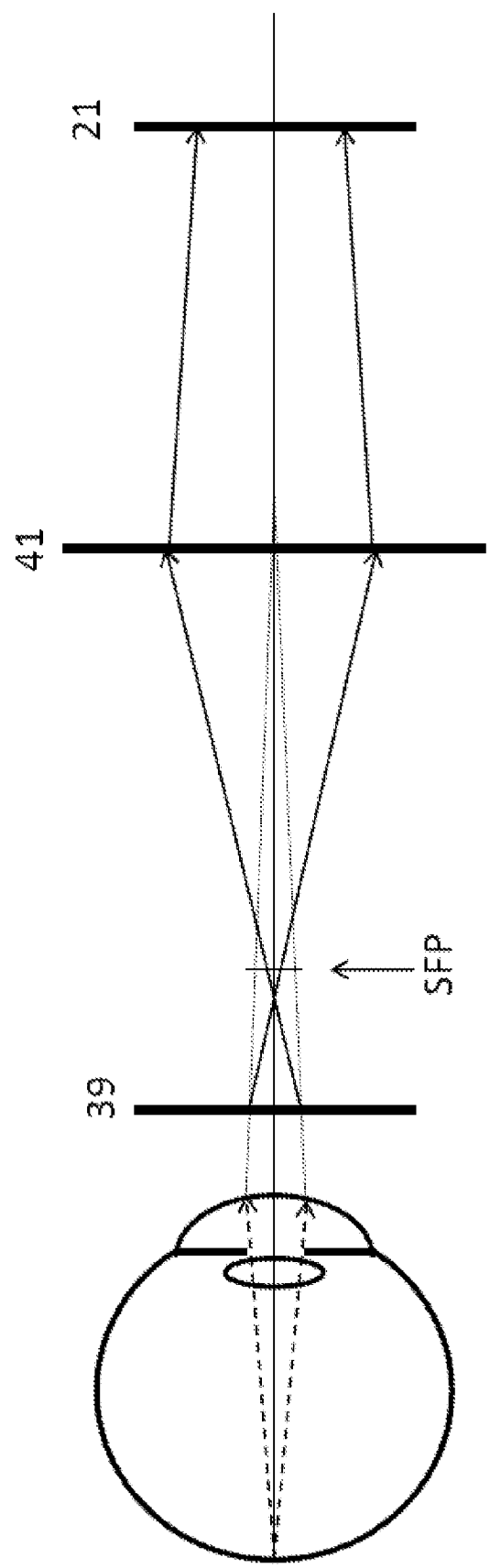
FIG. 17 shows a ray diagram demonstrating the effect of refractive error in the eye of a short sighted person relative to the optical system of the adaptor.
Figure 18:
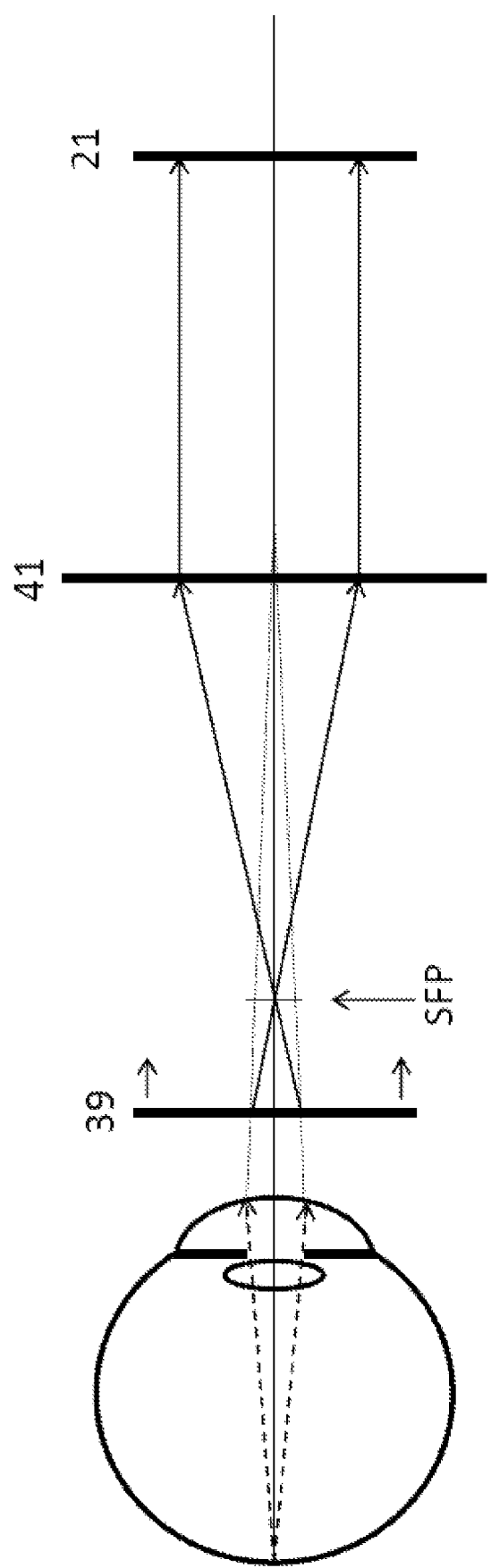
FIG. 18 shows a ray diagram demonstrating adjustment of the position of the objective lens relative to the secondary lens of the adaptor to account for refractive error in a short sighted person in order to capture a focussed image using the smartphone.

Referring to FIG. 17, for a patient with −20 dioptres of myopia (extreme short sightedness), the image of the retina 9 emerges from the eye 1 as convergent rays which focus at a point located 50 mm to the right of the cornea 3. Again, assuming the adaptor 17 is arranged such that the objective lens 39 is positioned 10 mm from the pupil 5 and 6 mm from the cornea 3, the image of the retina 9 appears as a real image located 44 mm to the right of the objective lens 39. Applying the thin lens equation (1/10=−1/44+1/image distance), the intermediate image is located approximately 8.1 mm to the right of the objective lens 39. Thus, the intermediate image is formed approximately 1.9 mm to the left of the front focal point SFP of the secondary lens 41. Consequently, the light rays relating to this image emerge as converging rays upon passing through the secondary lens 41 and continue as converging rays into the smartphone lens 21. Since the lens 21 is unable to focus converging rays at the sensor, it is difficult or impossible for the smartphone camera to adjust its lens so as to capture a sharp image of the retina 9. Thus, for a short sighted person, minor adjustment of the position of the objective lens 39 relative to the secondary lens 41 may be required to bring the intermediate image to a position that substantially coincides with the SFP of the secondary lens 41. In this particular example, therefore, as depicted in FIG. 18, the objective lens 39 position may be shifted approximately 2 mm closer to the secondary lens 41 in order to obtain a sharper image of the retina 9 with the smartphone camera.

When in use, the smartphone case 65 is attached to the smartphone 15 and the adaptor 17 is accurately positioned using the magnets 61, 63 such that the principal axis of the adaptor 17 is aligned with the optic axis of the camera aperture 19 and lens 21 of the smartphone 15. The light module 43 is activated with the switch 59 to provide illumination and the camera of the smartphone is turned on. The practitioner manoeuvres the combined fundus camera in proximity to the patient's eye 1 such that the focal point of the objective lens substantially coincides with the pupil plane and such that the tube extension 33 is directed toward the patient's pupil 5. Light waves from the light module 43 are directed into the eye 1 via the periphery of the pupil 5, thereby illuminating the eye interior and causing light to be reflected by the retina 9 out from the eye interior via the pupil 5. The reflected light emanating from the pupil 5 is received by the adaptor 17 via the tube extension aperture 37 where it is redirected by the objective lens 39 toward the secondary lens 41 and further focussed toward the camera aperture 19 and onto the sensor. The image of the patient's retina falling on the sensor is readily captured by the smartphone camera in live mode. Advantageously, no flash is required. Furthermore, no direct physical contact between the device and the patient's eye is required, thereby avoiding potential eye injury or spreading of infections. The image captured by the smartphone 15 may then be processed with appropriate smartphone software for storage, analysis and sharing. With the advent of pattern-recognition technology, auto-capture may be possible in the future with such a device.

Whilst no flash is required in the above described embodiment, in an alternative embodiment, it is envisaged the light source could be provided by the smartphone flash rather than a dedicated light module. For example, the housing may be adapted such that the first aperture or an additional aperture permits light from the flash of the smartphone to enter the tube of the adaptor. In such an embodiment, a polariser is arranged on the housing to extend across the region of entry of light from the flash into the tube so as to polarize light from the flash entering the tube. In this embodiment, since no dedicated light module and, hence, no separate power source is required, such an embodiment may be simpler and cheaper to manufacture than the first described embodiment.

It is envisaged that the adaptor 17 could be used with other image acquisition devices or be incorporated into an image acquisition device specifically designed for fundus photography. For example, the adaptor 17 could form part of a more specialised piece of equipment for use during eye surgery.

Figure 19:
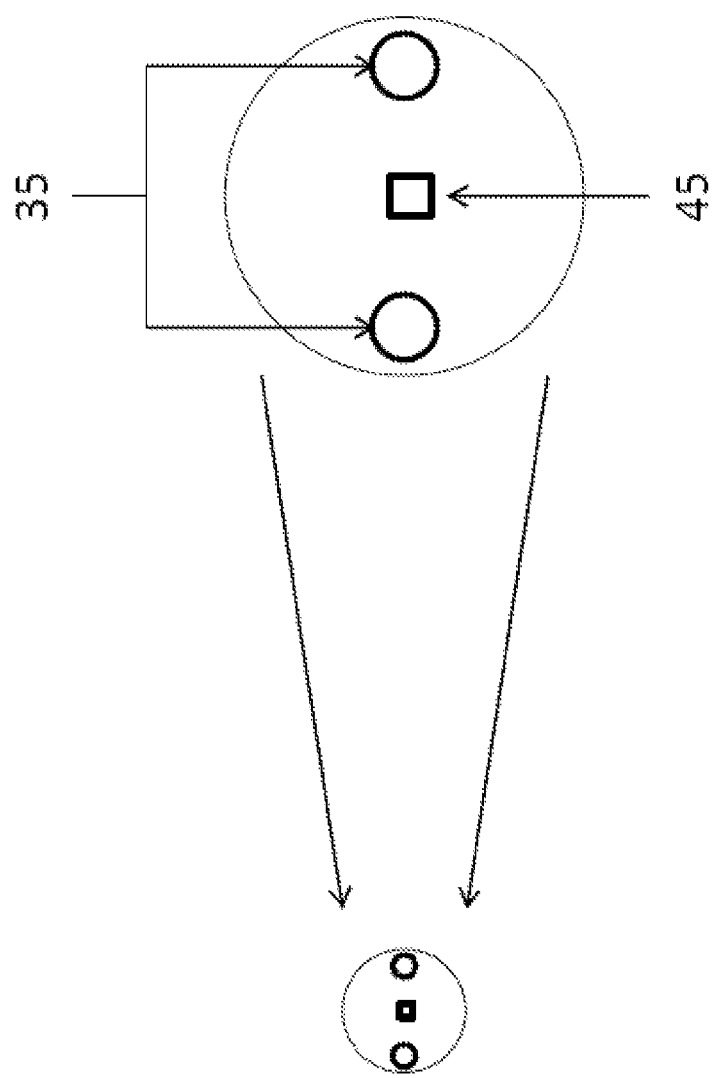
FIG. 19 shows a part of an alternative embodiment of an adaptor and its relationship to pupil size.

It is also envisaged that the adaptor 17 could be used with image acquisition devices comprising more than one camera aperture. For example, with reference to FIG. 19, the adaptor 17 could be used with image acquisition devices capable of capturing 3 dimensional images and videos. Provided the camera apertures and one or more light sources are configured to lie within the diameter of the magnified image of the pupil in proximity to the camera apertures, the adaptor 17 should be capable of illuminating the retina of an appropriately positioned eye and capable of enabling the image acquisition device to capture a 3-dimensional image of the retina. In such an embodiment, the light source may be arranged in between two camera apertures, all of which are arranged to lie within the diameter of the magnified pupil image at or about the plane of the camera apertures. For example, the adaptor 17 could be modified to comprise two base aperture 35 arranged either side of a centrally located light source 45. The relative positioning of the base apertures 35 may such that when the adaptor 17 is attached to a camera capable of stereoscopic image acquisition, the base apertures 35 are substantially aligned with a pair of camera apertures of the image acquisition device so that light may enter the camera apertures 35 via the adaptor 17.

With such an embodiment, the stereoscopic image acquisition device and adaptor will be capable of capturing two dissimilar images of the fundus which may be combined to form a stereoscopic image. The larger the separation between the camera apertures, the more dissimilar the images acquired will be.

It is envisaged that the adaptor could be modified to accommodate even more camera apertures of an acquisition device as dependent on the type of acquisition device to which the adaptor is intended to be attached. The adaptor could also be modified to include or accommodate any number of light sources for enhanced imaging and diagnostic capabilities. As above, the main requirement is that the light sources and camera apertures are arranged to be contained within the magnified image of the pupil produced by the optical system of the adaptor at or about the plane of the camera apertures.

Whilst the light sources can be placed anywhere in proximity to the camera apertures, they should preferably be placed as far from a camera aperture as possible but still within the confines of the magnified pupil image at or around the one or more camera apertures to minimise back scatter and glare that might arise at the pupil plane or corneal plane and that would otherwise interfere with the viewing pathway.

In addition, whilst a camera aperture should ideally be aligned with the principal axis of the optical system of the adaptor 17 for capturing the clearest image, even when the camera apertures are slightly offset from the principal axis, they should still be capable of capturing an image of the retina from received light travelling from the eye 1 along the viewing pathway. However, in this slightly offset arrangement the captured image may suffer from a degree of blurring at a side of the pupil image furthest from the camera aperture, although this may actually be advantageous for 3-dimensional image capture.

The above embodiments are described by way of example only. Many variations are possible without departing from the scope of the invention as defined in the appended claims.

What is claimed is:

1. An adaptor for attachment to an image acquisition device, the image acquisition device being a smartphone or tablet computer and having one or more camera apertures for enabling capture of one or more images entering the image acquisition device via the one or more camera apertures, the adaptor comprising
    a housing defining a passage, the housing configured to permit light waves to enter one or more camera apertures of the image acquisition device from the adaptor exterior via the passage and to permit light waves to exit the passage to the adaptor exterior,
    an objective lens arrangement within the passage having an optical axis, a front focal point, and a back focal point,
    a secondary lens arrangement within the passage having an optical axis, a front focal point, and a back focal point, the secondary lens arrangement positioned in the passage such that, when the adaptor is attached to an image acquisition device, the secondary lens arrangement is along a possible light pathway between the objective lens arrangement and one or more camera apertures of the image acquisition device,
    wherein a diameter of the secondary lens arrangement is greater than or equal to a diameter of the objective lens arrangement,
    wherein the objective lens arrangement and the secondary lens arrangement are together configured to magnify an image of a pupil of an eye in proximity to a plane of one or more camera apertures of the image acquisition device when the eye is not in contact with the adaptor and the pupil of the eye is positioned so that a plane of the pupil substantially coincides with the front focal point of the objective lens, the magnified image of the pupil having a diameter which is dependent on the respective focal lengths and relative spacing of the objective and secondary lenses, at least one of the one or more camera apertures positioned within the diameter of the magnified image when the adaptor is attached to an image acquisition device,
    and
    wherein the objective lens arrangement and the secondary lens arrangement are together configured to focus light waves from a light source directed into the passage toward the secondary lens from a position in proximity to one or more camera apertures, offset from the optical axis of the secondary lens and within the diameter of the magnified image of the pupil, said light waves focused at a point external of the adaptor and offset from the optical axis of the objective lens.

2. An adaptor as claimed in claim 1, further comprising the light source.

3. An adaptor as claimed in claim 2, wherein the light source comprises one or more light emitting diodes.

4. An adaptor as claimed in claim 1, wherein the light source is separate from the adaptor and the adaptor is configured to permit light from the light source to enter the passage.

5. An adaptor as claimed in claim 1, further comprising one or more polarizers associated with the light source to polarize light from the light source and one or more other polarizers arranged to filter light entering one or more camera apertures from the passage when the adaptor is attached to an image acquisition device.

6. An adaptor as claimed in claim 5, wherein the one or more polarizers associated with the light source polarizes light differently from the one or more other polarizers so that polarized light from the light source is filtered out by the one or more other polarizers.

7. An adaptor as claimed in claim 1, wherein the secondary lens arrangement is positioned such that, when the adaptor is attached to an image acquisition device, the back focal point of the secondary lens is located in proximity to the plane of one or more camera apertures of the image acquisition device so that the image acquisition device can focus the light waves received from the passage of the adaptor and capture one or more images.

8. An adaptor as claimed in claim 1, wherein the objective lens arrangement has a shorter focal length than the secondary lens arrangement.

9. An adaptor as claimed in claim 1, wherein the objective lens arrangement is positioned relative to the secondary lens arrangement such that the back focal point of the objective lens arrangement at least substantially coincides with the front focal point of the secondary lens arrangement.

10. An adaptor as claimed in any claim 1, wherein the objective lens arrangement is moveable relative to the secondary lens arrangement such that the position of the back focal point of the objective lens arrangement can be adjusted relative to the position of the front focal point of the secondary lens arrangement.

11. An adaptor as claimed in claim 1, wherein the objective lens arrangement and the secondary lens arrangement each comprise a condensing lens.

12. An adaptor as claimed in claim 11, wherein the objective condensing lens and the secondary condensing lens each comprise a pair of doublet lenses, for each pair, the doublet lenses being arranged such that their more convex sides face toward one another.

13. An adaptor as claimed in claim 1, further comprising means for attaching the adaptor to the image acquisition device.

14. A fundus photography system comprising:
a. an image acquisition device, the image acquisition device being a smartphone or tablet computer; and
b. an adaptor for attachment to an image acquisition device, the image acquisition device having one or more camera apertures for enabling capture of one or more images entering the image acquisition device via the one or more camera apertures, the adaptor comprising:
   i. a housing defining a passage, the housing configured to permit light waves to enter one or more camera apertures of the image acquisition device from the adaptor exterior via the passage and to permit light waves to exit the passage to the adaptor exterior,
   ii. an objective lens arrangement within the passage having an optical axis, a front focal point, and a back focal point,
   iii. a secondary lens arrangement within the passage having an optical axis, a front focal point, and a back focal point, the secondary lens arrangement positioned in the passage such that, when the adaptor is attached to an image acquisition device, the secondary lens arrangement is along a possible light pathway between the objective lens arrangement and one or more camera apertures of the image acquisition device,
   iv. wherein a diameter of the secondary lens arrangement is greater than or equal to a diameter of the objective lens arrangement,
   v. wherein the objective lens arrangement and the secondary lens arrangement are together configured to magnify an image of a pupil of the eye in proximity to a plane of one or more camera apertures of the image acquisition device when the eye is not in contact with the adaptor and the pupil of the eye is positioned so that a plane of the pupil substantially coincides with the front focal point of the objective lens, the magnified image of the pupil having a diameter which is dependent on the respective focal lengths and relative spacing of the objective and secondary lenses, at least one of the one or more camera apertures positioned within the diameter of the magnified image when the adaptor is attached to an image acquisition device, and
   vi. wherein the objective lens arrangement and the secondary lens arrangement are together configured to focus light waves from a light source directed into the passage toward the secondary lens from a position in proximity to one or more camera apertures, offset from the optical axis of the secondary lens and within the diameter of the magnified image of the pupil, said light waves focussed at a point external of the adaptor and offset from the optical axis of the objective lens.

15. A fundus photography system as claimed in claim 14, wherein the image acquisition device is associated with a mounting device comprising means for attaching the adaptor to the mounting device to hold the adaptor in a position relative to the image acquisition device at which an optic axis of the adaptor is at least substantially aligned with an optic axis of the camera aperture.

16. A fundus photography system as claimed in claim 15, wherein the mounting device comprises a protective case for attachment to the image acquisition device.

17. A fundus photography system as claimed in claim 15, wherein the means for attaching comprises one or more magnets.

18. A method of using a fundus photography system comprising an image acquisition device, the image acquisition device being a smartphone or tablet computer and having one or more camera apertures for enabling capture of one or more images entering the image acquisition device via the one or more camera apertures, and an adaptor for attachment to an image acquisition device, the image acquisition device, the adaptor comprising: a housing defining a passage, the housing configured to permit light waves to enter one or more camera apertures of the image acquisition device from the adaptor exterior via the passage and to permit light waves to exit the passage to the adaptor exterior;

an objective lens arrangement within the passage having an optical axis, a front focal point, and a back focal point; a secondary lens arrangement within the passage having an optical axis, a front focal point, and a back focal point, the secondary lens arrangement positioned in the passage such that, when the adaptor is attached to an image acquisition device, the secondary lens arrangement is along a possible light pathway between the objective lens arrangement and one or more camera apertures of the image acquisition device; wherein a diameter of the secondary lens arrangement is greater than or equal to a diameter of the objective lens arrangement; wherein the objective lens arrangement and the secondary lens arrangement are together configured to magnify an image of a pupil of the eye in proximity to a plane of one or more camera apertures of the image acquisition device when the eye is not in contact with the adaptor and the pupil of the eye is positioned so that the pupil plane substantially coincides with the front focal point of the objective lens, the magnified image of the pupil having a diameter which is dependent on the respective focal lengths and relative spacing of the objective and secondary lenses, at least one of the one or more camera apertures positioned within the diameter of the magnified image when the adaptor is attached to an image acquisition device; and wherein the objective lens arrangement and the secondary lens arrangement are together configured to focus light waves from a light source directed into the passage toward the secondary lens from a position in proximity to one or more camera apertures, offset from the optical axis of the secondary lens and within the diameter of the magnified image of the pupil, said light waves focussed at a point external of the adaptor and offset from the optical axis of the objective lens, wherein the method comprises the steps of:

a. arranging the system such that the adaptor is not in contact with the eye and the front focal point of the objective lens substantially coincides with a plane of the pupil of the eye and such that the centre of the pupil is substantially aligned with the optical axis of the objective lens, b. directing light into the passage toward the secondary lens from a position in proximity to one or more camera apertures of the image acquisition device, offset from the optical axis of the secondary lens and within the diameter of the magnified image of the pupil, and c. capturing with the image acquisition device an image of a retina of the eye received by the image acquisition device from the eye interior via the adaptor.

* * * * *